(12) United States Patent
Kunis

(10) Patent No.: US 11,419,633 B2
(45) Date of Patent: *Aug. 23, 2022

(54) TRANSSEPTAL ACCESS DEVICE AND METHOD OF USE

(71) Applicant: Christopher Gerard Kunis, Escondido, CA (US)

(72) Inventor: Christopher Gerard Kunis, Escondido, CA (US)

(73) Assignee: Mark D. Wieczorek, PC, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/480,385

(22) Filed: Sep. 21, 2021

(65) Prior Publication Data

US 2022/0001102 A1 Jan. 6, 2022

Related U.S. Application Data

(60) Continuation of application No. 16/282,366, filed on Feb. 22, 2019, which is a continuation of application
(Continued)

(51) Int. Cl.
*A61B 17/34* (2006.01)
*A61M 5/00* (2006.01)
(Continued)

(52) U.S. Cl.
CPC ........... *A61B 17/3478* (2013.01); *A61M 5/00* (2013.01); *A61M 5/158* (2013.01); *A61M 25/00* (2013.01);
(Continued)

(58) Field of Classification Search
CPC . A61M 5/00; A61M 25/0082; A61B 1/00089; A61B 2017/306; A61B 17/3478;
(Continued)

(56) References Cited

U.S. PATENT DOCUMENTS 5,282,815 A * 2/1994 Kabbara ................. A61F 9/013
606/166
2007/0287886 A1* 12/2007 Saadat ................. A61B 5/6882
600/115
(Continued)

FOREIGN PATENT DOCUMENTS

CN 108472475 A * 8/2018 ......... A61B 1/00082

*Primary Examiner* — Katherine M Shi
(74) *Attorney, Agent, or Firm* — Mayer & Williams, PC

(57) ABSTRACT

Systems, devices, and methods are provided for transseptal access of septa within a patient. The device can be advanced to a septum, e.g., towards a fossa ovalis. Instead of applying positive pressure to "tent" the septum, a negative pressure is applied to a lumen within a sheath, e.g., within an elongated member slidable within the sheath, via a negative pressure source such as a syringe on the proximal end of the sheath. This results in the septum pulling inward. The sheath employs a stationary needle-like central core component contained within the lumen of the sheath that punctures the septum when the same is pulled passed it by the negative pressure. The stationary needle-like central core component may be hollow and may form a portion of the elongated member or may be coupled to a distal end thereof.

17 Claims, 24 Drawing Sheets

Related U.S. Application Data

No. 14/667,155, filed on Mar. 24, 2015, now Pat. No. 10,220,134, which is a continuation-in-part of application No. 14/567,427, filed on Dec. 11, 2014, now Pat. No. 10,307,569, which is a division of application No. 13/093,546, filed on Apr. 25, 2011, now Pat. No. 8,940,008.

(60) Provisional application No. 61/969,453, filed on Mar. 24, 2014, provisional application No. 61/443,483, filed on Feb. 16, 2011, provisional application No. 61/359,674, filed on Jun. 29, 2010, provisional application No. 61/327,542, filed on Apr. 23, 2010.

(51) Int. Cl.
| | | |
|---|---|---|
| *A61M 5/158* | (2006.01) | |
| *A61M 25/00* | (2006.01) | |
| *A61B 17/30* | (2006.01) | |
| *A61M 25/06* | (2006.01) | |
| *A61B 90/00* | (2016.01) | |
| *A61B 17/00* | (2006.01) | |

(52) U.S. Cl.
CPC .............. *A61M 25/0074* (2013.01); *A61B 2017/00247* (2013.01); *A61B 2017/306* (2013.01); *A61B 2090/064* (2016.02); *A61B 2090/0807* (2016.02); *A61M 25/0082* (2013.01); *A61M 2005/1585* (2013.01); *A61M 2025/0681* (2013.01)

(58) Field of Classification Search
CPC ......... A61B 1/0008; A61B 1/018; A61B 1/04; A61B 2017/0024; A61B 2017/00247
See application file for complete search history.

(56) References Cited

U.S. PATENT DOCUMENTS

| | | | | |
|---|---|---|---|---|
| 2007/0293724 | A1* | 12/2007 | Saadat | A61B 1/00085 600/156 |
| 2008/0009747 | A1* | 1/2008 | Saadat | A61B 1/00089 604/510 |
| 2011/0264072 | A1* | 10/2011 | Kunis | A61M 25/0082 604/506 |
| 2012/0239069 | A1* | 9/2012 | Benscoter | A61B 17/3478 606/185 |
| 2013/0296879 | A1* | 11/2013 | Lazeroms | A61N 1/0587 606/129 |
| 2014/0358089 | A1* | 12/2014 | Kappel | A61B 1/00089 604/176 |

* cited by examiner

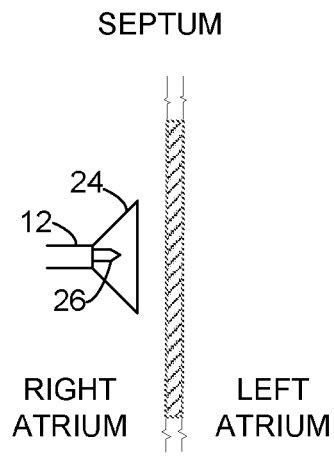
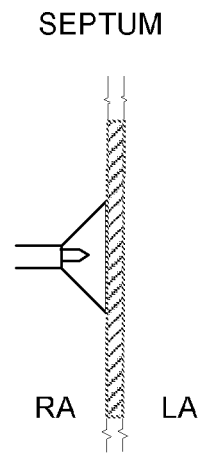
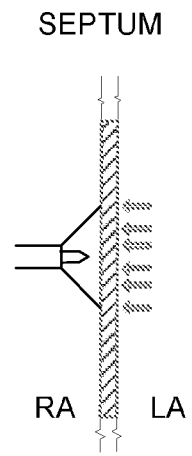
FIG. 2(A)          FIG. 2(B)          FIG. 2(C)
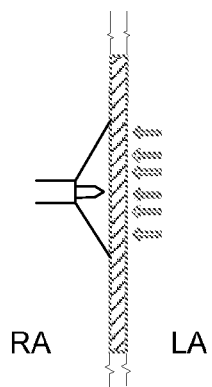
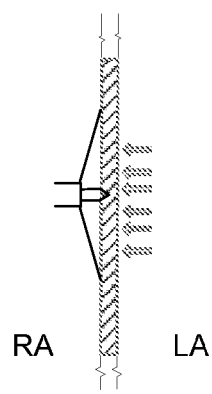
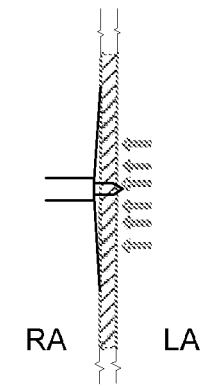
FIG. 2(D)          FIG. 2(E)          FIG. 2(F)
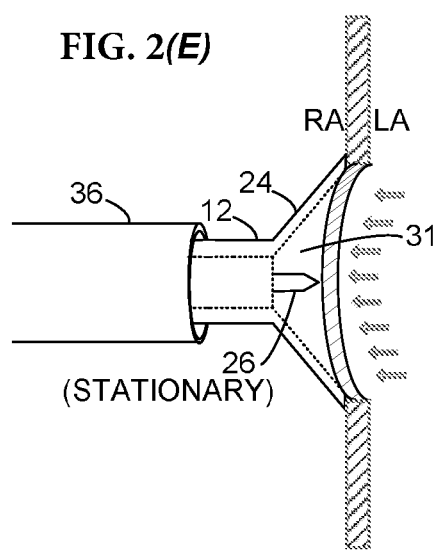
FIG. 2(G)

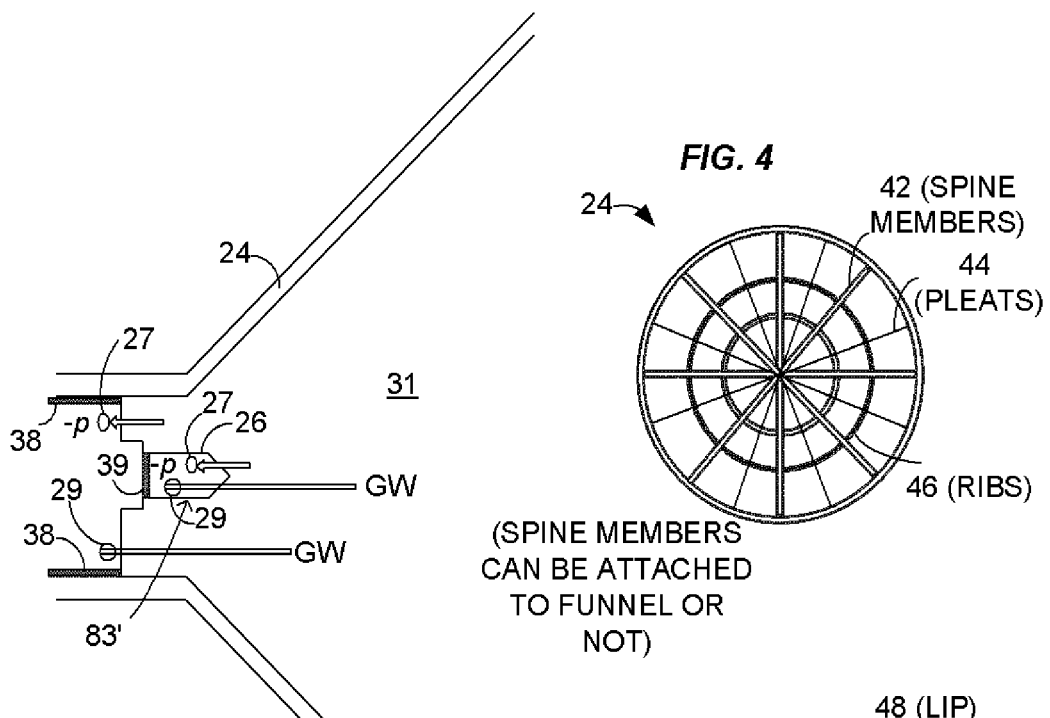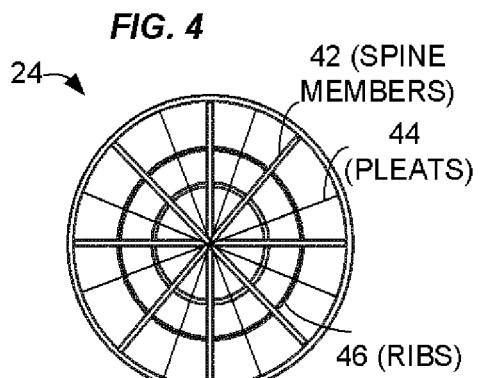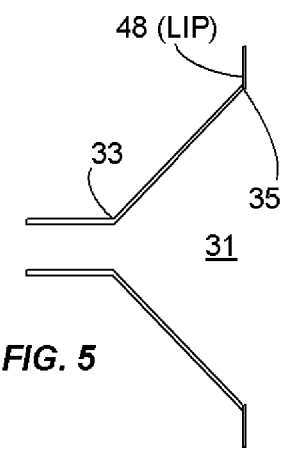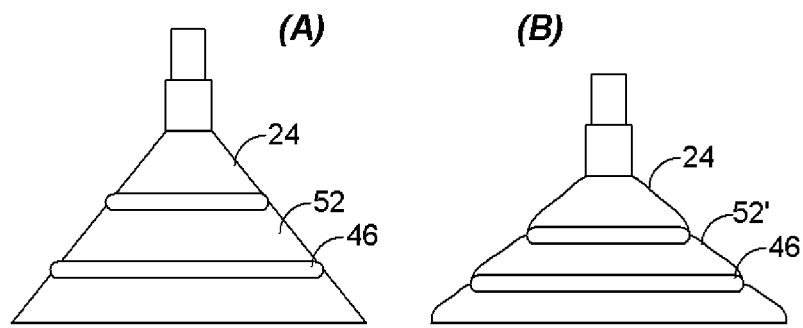

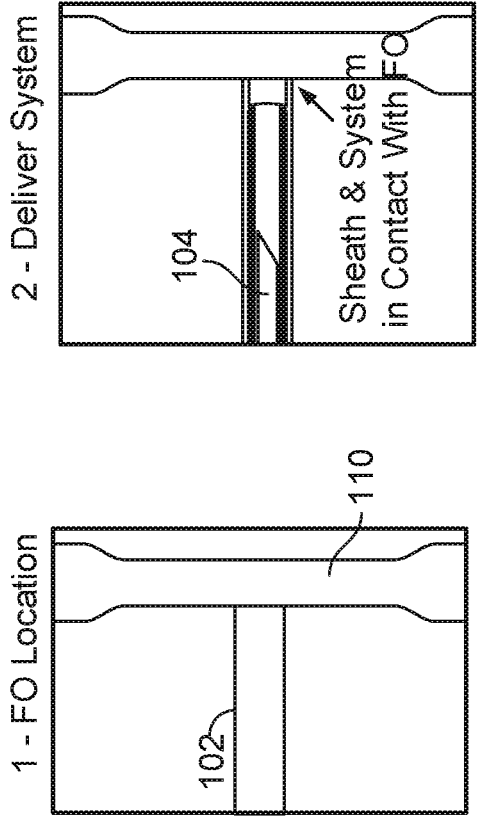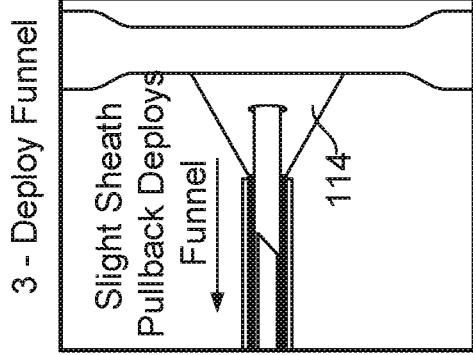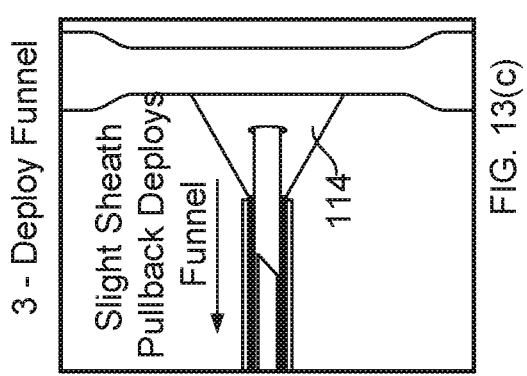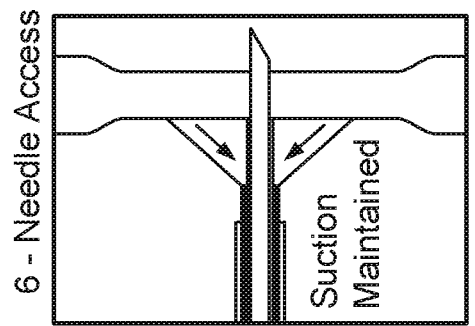

TRANSSEPTAL ACCESS DEVICE AND METHOD OF USE

CROSS-REFERENCE TO RELATED APPLICATIONS

This application is a continuation of U.S. Ser. No. 16/282,366, filed Feb. 22, 2019, which is a continuation of U.S. Ser. No. 14/667,155, filed Mar. 24, 2015, entitled, "TRANSSEPTAL ACCESS DEVICE AND METHOD OF USE" which is a Continuation in Part of U.S. Ser. No. 14/567,427, filed Dec. 11, 2014, entitled, "TRANSSEPTAL ACCESS DEVICE AND METHOD OF USE" and also claims benefit of priority of U.S. Provisional Patent Application Ser. No. 61/969,453, filed Mar. 24, 2014, entitled "SYSTEMS AND METHODS FOR PROVIDING ATRAUMATIC ACCESS THROUGH TISSUES"; U.S. Ser. No. 14/567,427 is a Divisional of Ser. No. 13/093,546, filed Apr. 25, 2011, now U.S. Pat. No. 8,940,008 issued Jan. 27, 2015, entitled "TRANSSEPTAL ACCESS DEVICE AND METHOD OF USE"; which claims benefit of priority to U.S. Provisional Patent Application No. 61/327,542, filed Apr. 23, 2010, entitled "TRANSSEPTAL ACCESS DEVICE AND METHOD OF USE", U.S. Provisional Patent Application No. 61/359,674, filed Jun. 29, 2010, entitled "TRANSSEPTAL ACCESS DEVICE AND METHOD OF USE, and U.S. Serial Provisional Patent Application No. 61/443,483, filed Feb. 16, 2011, entitled "TRANSSEPTAL ACCESS DEVICE AND METHOD OF USE"; all of the above are herein incorporated by reference in their entirety.

BACKGROUND

In many procedures, it is necessary to obtain access through bodily tissues. For example, in many cardiac procedures it is necessary to obtain access through the cardiac septum. Prior efforts to obtain access include piercing a small hole in the septal wall, typically at a location called the fossa ovalis ("FO"). Such access is term transseptal ("TS") access.

TS access is often performed by delivering a sheath/dilator through the venous bed into the right atria and to the septal wall. With the tip of the dilator dragged along the septal wall, the same is dragged to the location of the FO. The sheath is then slightly advanced forward, applying pressure to the FO, creating what is called "tenting" of the FO. A long TS needle, e.g., a "Brockenbrough or "BB" needle, is then advanced through the lumen of the dilator that is inserted through the sheath. The needle is advanced against the FO while it is tented. The needle then punctures through the FO and into the left atrium.

The TS needle may be hollow or may incorporate a guide wire lumen to enable fluid delivery, and/or a guide wire or other minimally invasive tools to be threaded through and into the left atrium of the heart. Once the guide wire is passed through the TS needle into the left atrium, the needle, dilator, and sheath maybe retracted while the guide wire remains in the left atrium for subsequent procedures.

In about 20% of TS cases, there is difficulty obtaining TS access because of highly fibrosed tissue from previous TS procedures. Additionally, the TS sheath and the BB needle, as the same are being pushed forward by a physician, often slide up or down instead of the needle moving forward to penetrate the tissue, increasing the tension on the FO, causing the same to tent further adding additional stress to the target tissue, again while the needle attempts to penetrates the tissue. In other cases, if the septum is heavily fibrotic, significant pressure is required to advance the TS needle into the left atrium. Both cases occasionally cause puncture of the opposite wall of the left atrium by the sudden exertion of the needle through the septum and subsequent perforation, causing a severe adverse event and potential for death. To address this several currently marketed TS devices require Radio Frequency (RF) delivered to the needle to penetrate said target tissue in heavily fibrosed septums.

SUMMARY

The current invention provides a system and method for achieving TS access while minimizing complications associated with obtaining TS access. In one implementation, the system includes a device that at least in part replaces the dilator and/or the needle. The device has a flared distal end, e.g., with a funnel-shaped polymer element that is radiopaque attached to the distal portion of a dilator element or needle, and within the flared distal end, a vacuum, suction, or other negative pressure may be applied. Also within the flared distal end is a center core section equipped with a pointed feature like a needle. With the use of a syringe or other source of negative pressure connected to the proximal end of the device, negative pressure is applied and the funnel tip prolapses, pulling the FO towards the stationary needle feature, puncturing the FO and obtaining access to the LA. A guidewire may then be advanced through a hollow portion of the puncturing feature of the TS access device for subsequent procedures.

In one aspect, the invention is directed to a method of gaining access through a septum, including: delivering a device to a selected location at a septum, the device including a funnel with a proximal end and a distal end and an interior therebetween, the distal end having a greater radius than the proximal end; placing the distal end of the funnel against the selected location; drawing a negative pressure in the interior, such that a portion of the septum and selected location are pulled within the interior of the device; and continuing to draw a negative pressure in the interior until an indication is received that the septum has been pulled past a stationary needle disposed within the interior.

Implementations of the invention may include one or more of the following. Upon receipt of the indication, the negative pressure may be increased to zero or a lumen in which the negative pressure was drawn may be valved off. The drawing a negative pressure may include coupling a syringe to a lumen, the lumen in pressure communication with the interior, and pulling back on a plunger of the syringe. The selected location may be a fossa ovalis. The negative pressure drawn may be between about that drawn by a 5 cc syringe and that drawn by a 100 c syringe, and even more between about that drawn by a 10 cc syringe and that drawn by a 20 cc syringe. The indication may be a presence of blood in a lumen in which the negative pressure was drawn or a reduction in the amount of negative pressure drawn. The method may further include inserting a guide wire through the device such that a distal tip of the guide wire is disposed in a desired location of the heart.

In another aspect, the invention is directed to a non-transitory computer readable medium, comprising instructions for causing a computing device to perform the above method.

In yet another aspect, the invention is directed to a device for transseptal access, including: an elongated member having a proximal end and a distal end, and a piercing element disposed at the distal end; and a funnel coupled to the elongated member at the distal end, the funnel having a proximal end with a first radius and a distal end with a second radius, the second radius greater than the first radius, the funnel having a retracted configuration and an expanded configuration, the expanded configuration defining an interior; and the device is such that the elongated member, the needle, and the funnel are configured to be delivered to a septal location through a transseptal sheath, and such that upon removal of the funnel from the sheath, the funnel assumes the expanded configuration, and such that a pressure lumen is defined in the elongated member extending from the proximal end and into the interior of the funnel.

Implementations of the invention may include one or more of the following. The first radius may be between about 3 French to 10 French, and the second radius may be between about 2.5 mm to 15 mm. Even more, first radius may be between about 5 French to 8 French, and the second radius may be between about 5 mm to 10 mm. The device may further include a fitting attached to the pressure lumen at the proximal end of the elongated member, the fitting configured to attach a negative pressure source thereto. The fitting may be configured to attach a syringe thereto. The funnel may further comprise a lip formed at the distal end. The negative pressure source may be configured to draw a negative pressure of between about that drawn by a 5 cc syringe and that drawn by a 100 c syringe, and even more between about that drawn by a 10 cc syringe and that drawn by a 20 cc syringe. The funnel may further include a rib, a spine member, or a pleat. The spine member may be attached to the funnel or not. The funnel may have a straight shape or a convoluted shape. The elongated member may have further defined a guidewire lumen therein, the guidewire lumen extending from the proximal end and into the interior of the funnel. In the retracted configuration, the funnel may substantially surround the stationary needle. In the expanded configuration, the funnel distal end may extend further in a distal direction than does the piercing element. The piercing element may be a stationary needle coupled to the elongated member at the distal end. The piercing element may be a dilator with a sharp tip. The funnel may be formed of a shape memory material, such as a polymer, and the rib or spine member may be comprised of a shape memory metal. The shape memory metal may be nitinol.

Advantages of the invention may include one or more of the following. The chance of pucture of cardiac walls is reduced by pulling in the FO with the negative pressure towards a stationary needle. This system may be combined with other devices, e.g., with a needle tip that curls after puncture, for an especially safe procedure. Another safety feature is that during delivery of the TS Access device, the funnel-shaped polymer element may be caused to collapse around the needle or penetrating, piercing, or puncturing element during delivery thru the sheath, protecting the needle from skiving the inner surface of the sheath while being delivered to the target location.

Other advantages will be apparent from the description that follows, including the figures and claims.

BRIEF DESCRIPTION OF THE DRAWINGS

FIGS. 2(A)-(G) illustrates side schematic views of a transseptal access system according to an implementation of the present invention, showing steps of the use of the system in penetrating a septum.

FIG. 3 illustrates a side schematic view of a transseptal access system according to an implementation of the present invention, particularly showing exemplary locations through which negative pressure may be applied, as well as guidewire lumen locations.

FIG. 4 illustrates an end-on view of a of a transseptal access system according to an implementation of the present invention, showing spine members, pleats, and ribs.

FIG. 5 illustrates a side schematic view of a transseptal access system according to an implementation of the present invention, showing a lip providing an enhanced coupling to the septum of some patients.

FIG. 6(A)-(B) illustrate side views of a ribbed funnel, illustrating straight sides (A) and convoluted sides (B). Other types of funnels may also be employed.

FIGS. 13A-13F illustrate steps in deployment of a device according to present principles.

Like reference numerals refer to like elements. Elements are not to scale unless otherwise noted.

DETAILED DESCRIPTION

U.S. patent application Ser. No. 13/093,546, now U.S. Pat. No. 8,940,008, owned by the assignee of the present application and herein incorporated by reference in its entirety, describes various systems and methods by which atraumatic TS access may be obtained. This application describes further such implementations of systems and methods.

Implementations of the device and method include a device that can be advanced to a septum, e.g., towards a FO. In this exemplary implementation, instead of applying positive pressure to "tent" the FO toward the LA, a negative pressure is applied to a lumen within the sheath, e.g., within an elongated member slidable within the sheath, via a negative pressure source such as a syringe on the proximal end of the sheath. This results in the FO pulling inward. The sheath employs a stationary needle-like central core component contained within the lumen of the sheath that punctures the FO when the same is pulled passed it by the negative pressure. The stationary needle-like central core component may be hollow and may form a portion of the elongated member or may be coupled to a distal end thereof.

After the puncture occurs, a guidewire may be threaded through the puncture and into the LA. The negative pressure creates a stable base for the TS puncture to occur. Moreover, by reversing the prior art process (by pulling the FO past the needle contained within the sheath), the chance of perforation is significantly reduced if not eliminated during TS procedures. In an alternative embodiment, the design may also incorporate ultrasound or other technology within the funnel shaped structure to enable better visualization of the FO prior to the puncture process to further eliminate perforation of adjacent structures. A pressure sensor located at the tip of the needle-like feature may also provide real-time feedback to the user to verify TS access has been achieved. The same may also provide information regarding the level of tension on the FO. Furthermore, a ring of electrodes affixed to the rim of the funnel feature configured in a uni-polar and or bi-polar configuration may also be adapted to further assist alignment and tissue contact of the device prior to crossing the septum. The device may be of a fixed curve (in a number of sizes and radii of curvature) or steerable sheath design and may include variations in length and diameter for various applications.

Figure 1:
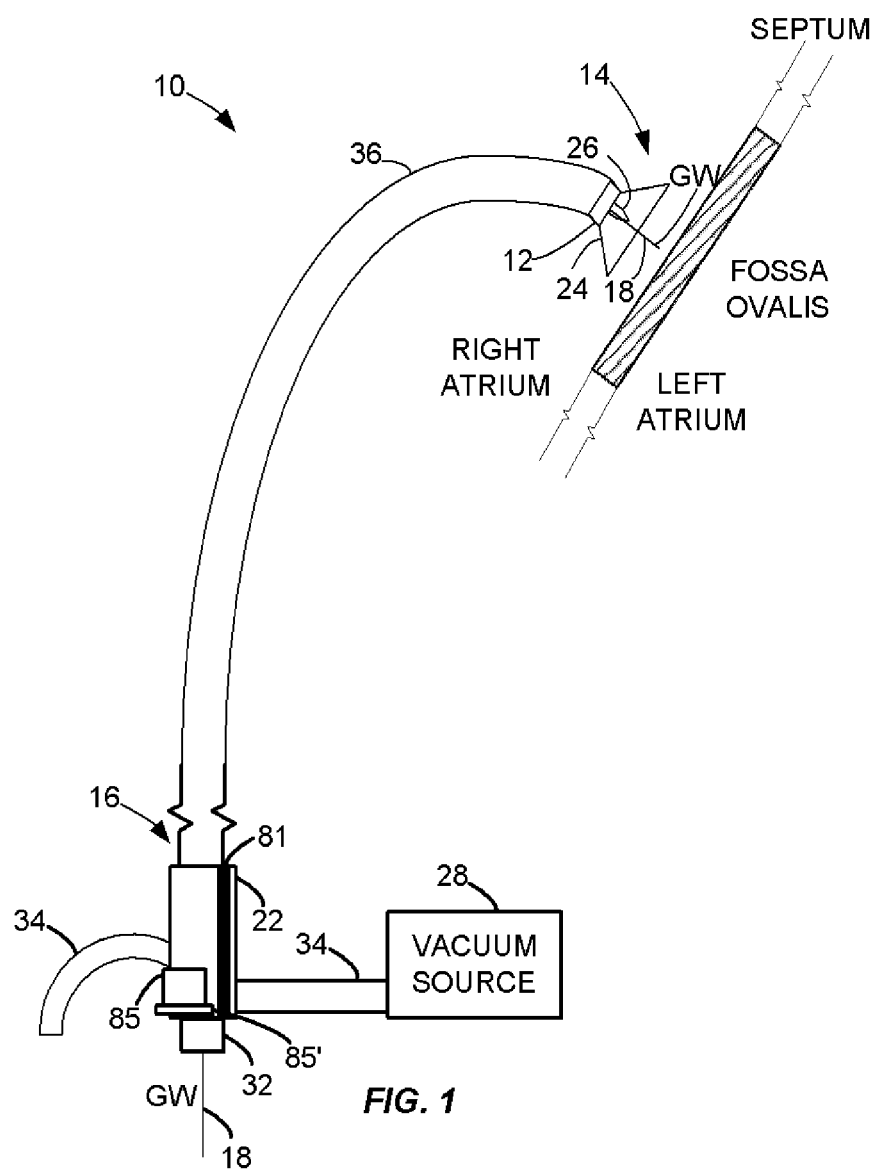
FIG. 1 illustrates a schematic view of a transseptal access system according to an implementation of the present invention.

FIG. 1 illustrates one implementation of the current device. A device 10 has a proximal end 16 and a distal end 14. The device 10 includes a funnel 24 extending from an elongated member 12 that slides within a standard TS sheath 36. The TS sheath 36 may be, e.g., an 8 French sheath. In FIG. 1, the funnel is shown in an expanded configuration. However, when within the sheath 36, the funnel is in a retracted configuration. In use, the funnel 24 is configured to engage a FO using a source such as a syringe at the proximal end 16 of the device. A negative pressure or vacuum is drawn to pull in the FO to the piercing element or needle 26, enabling access to the LA. That is, the FO is pulled toward the piercing element or needle and eventually the FO is pulled past the piercing element or needle, causing the piercing element or needle to penetrate the FO. It is noted that the piercing element or needle may be stationary with respect to the sheath, the guide wire, and/or the remainder of the heart. It is the FO that may be caused to move in a direction so as to be penetrated by the piercing element or needle; the FO need not be actively penetrated by a moving needle or piercing element.

FIGS. 2 (A)-(F) illustrate the above movement of the funnel 24 and FO of the septum past the stationary needle or piercing element 26 and elongated member 12, which may be generally a catheter main body polymer tubing. In (A), the device is situated away from the septum, but the funnel has been extended past the sheath and thus is in a flared or expanded configuration. In (B), the device abuts the septum, but no negative pressure has yet been drawn. In (C), a negative pressure or vacuum begins to pull on the septum, e.g., the FO, such as by a syringe or pump which is in pressure communication with an interior 31 of the funnel. In (D), the negative pressure increases, and the funnel 24 begins to flare out even more. It is noted in this regard that in FIGS. 2 (A)-(F), the movement of the septum is not shown; it is however shown in FIG. 2 (G). In (E), the funnel 24 flares out even more as the septum is pulled towards the needle, and in this figure the needle or piercing element 26 begins to pierce the septum. In (F), the FO has completely moved past the needle 26 because of the applied negative pressure. As noted above, FIG. 2(G) illustrates schematically the movement of the septum, e.g., the FO, towards the stationary needle 26, as a result of the drawn negative pressure.

FIG. 3 illustrates additional details of the distal tip of the elongated member 12, including the funnel 24. In particular, the distal tip 14 of the elongated member 12 is illustrated with the funnel 24 in the expanded configuration. The funnel may be seen to be coupled to the elongated member 12 by virtue of a bond 38. Another bond 39 may be employed to attach the needle or piercing element 26 to the distal tip 14 of the elongated member 12.

Negative pressure may be drawn by one or more vacuum or pressure lumens 27, while one or more guide wire lumens 29 may be employed to pass a guide wire, e.g., into the LA of the heart. Of course, it will be understood that in any given implementation only one guide wire lumen may be required. One or more pressure lumens may be employed to draw the negative pressure, pulling the septum past needle or piercing element 26.

Referring back to FIG. 1, a hemostasis valve 32 may be employed to seal the handle, so as to allow a vacuum and yet enable the user to advance and retract the guide wire during use. A handle 22 is located on the proximal end of the TS access device. A side port tube 34 and syringe hub may be connected to the handle, providing fluid exchange with the inner lumens of the TS access device. Such facilities allow the user to aspirate the lumen to create a vacuum against the septum of the heart, e.g., at the FO, or at other locations along the septum.

Referring to FIG. 4, an end-on view is illustrated of the funnel 24. A number of elements may be employed to enhance the structural integrity of the funnel 24, although not all elements need be employed in every situation, and in many cases no such elements may be employed. First, to assist in the flaring of the funnel, spine members 42 may be employed. The spine members 42 may be attached to the funnel or not, but in any case provide a degree of spring action to flare or fan out the funnel when the same is outside of the sheath. A number of pleats 44 may be employed, the same allowing the funnel to flare out. A number of circumferential ribs 46 may also be employed to assist in the shaping of the flared funnel 24, and these ribs 46 are further discussed below. The spine members and rib members may be made of nitinol wire. However, the polymer of the funnel alone may be designed so as to have memory as well and/or an inherent geometric shape, which may incorporate the pleats noted above, to help the polymer funnel element to deploy into the funnel shape.

In FIG. 4 it is noted that the funnel may be of a soft durometer polymer and can include an additive providing a radio-opaque feature for visualization under fluoroscopy. The flared tip may be soft, thin-walled, and designed to prolapse during application of vacuum, allowing the FO to be forced into contact with the piercing element or needle. In another implementation, the needle may be attached to a mechanism that can be advanced following vacuum application to the FO allowing a controlled perforation of the septum.

As noted above, the piercing element or needle may be bonded to the inside surface of the TS access device. The piercing element or needle may be of a hollow design. After the puncture of the septum occurs, a guidewire can then be advanced through the hollow piercing element or needle through guidewire lumen 29, and advanced into the LA thru the puncture provided.

FIG. 5 illustrates that the funnel 24 may have a lip 48 disposed at a distal end thereof, the lip circumferentially surrounding the funnel 24. The lip 48 provides an even greater attachment of the funnel 24 to the septum. This figure also shows the proximal end 33 and a distal end 35 of the funnel 24.

FIG. 6 (A)-(B) illustrate that the funnel 24, including ribs 46, may have a straight conical profile 52 or may have a convoluted profile 52'. In some implementations, the convoluted profile 52' allows for easier folding into the sheath 36 as well as enhanced attachment to the septum.

Figure 7:
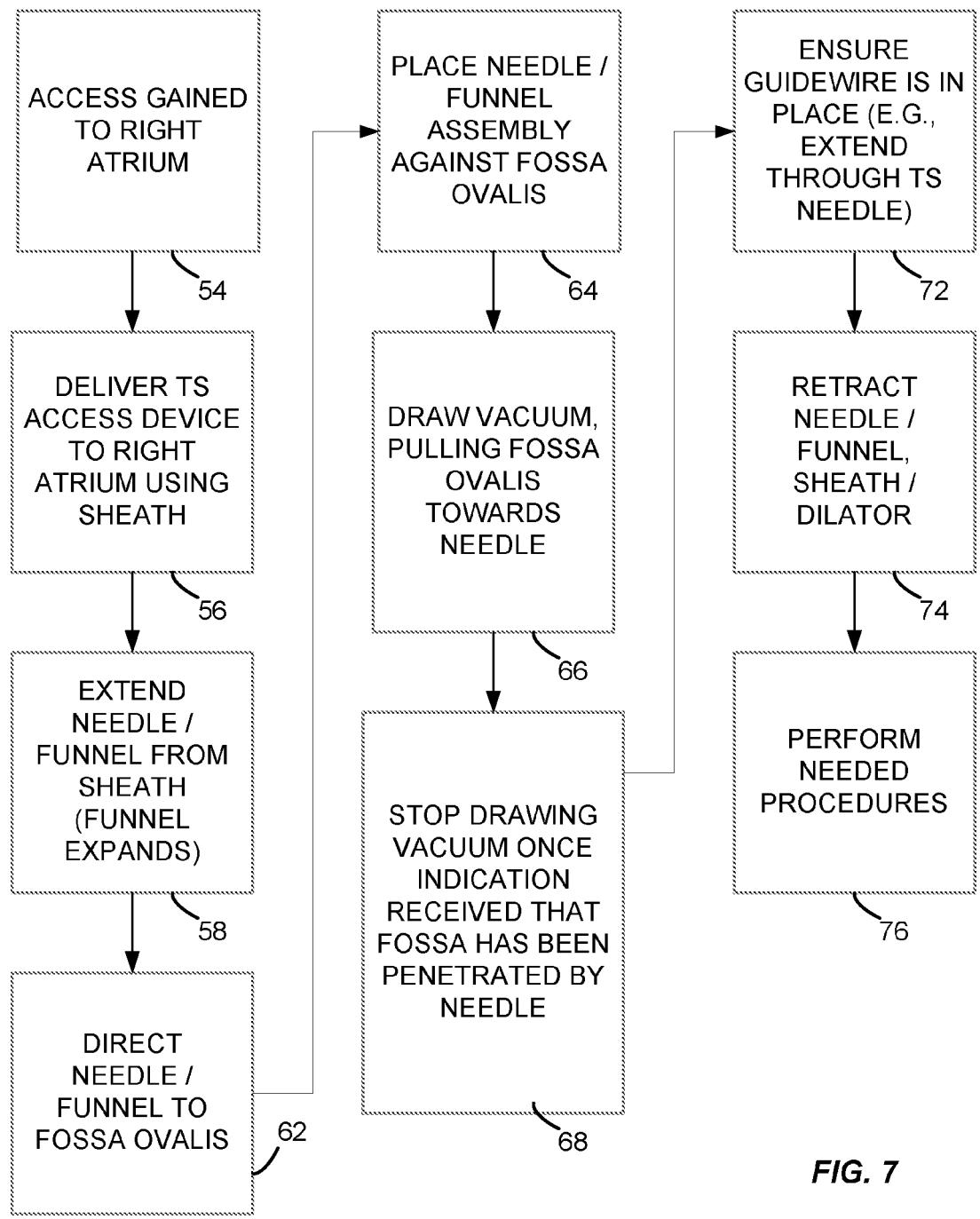
FIG. 7 is a flowchart illustrating a method according to an implementation of the present invention.

FIG. 7 illustrates a flowchart embodying a method of the invention. In a first step, access is gained to the right atrium (step 54). In this step, a femoral or other vein is accessed, allowing movement of devices towards the heart and into the right atrium through the inferior vena cava. A next step is to deliver the TS access device to the right atrium using a sheath (step 56). The needle and funnel are extended from the sheath, causing the funnel to expand by virtue of its own memory element, memory metal in spine or other members, or both. A next step is that the needle and funnel are directed towards the septum, and commonly towards the FO (step 62). A next step is the placement of the needle and funnel assembly against the FO (step 64). A next step is to draw a vacuum or negative pressure, pulling the FO towards the needle (step 66). The vacuum or negative pressure may be drawn using any of the methods described above, including by use of a syringe or micro pump. A next step is to stop the negative pressure drawing once an indication has been received that the FO has been penetrated by the needle (step 68). The indication may be by the detection of the presence of blood in the lumen that draws the negative pressure, a reduction in the measured negative pressure, or the like. Where a reduction in the negative pressure is used, a measurement device may be employed to measure the pressure during the drawing step. A next step is to ensure that a guide wire is in place, e.g., by extending the same through the needle (step 72). A next step is to retract the needle and funnel, as well as the sheath and any dilator that may have been used (step 74). The procedures requiring TS access may then be performed (step 76).

The device significantly improves the safety profile of such procedures, simplifies the same, and reduces the time needed to achieve LA access.

Figure 8:
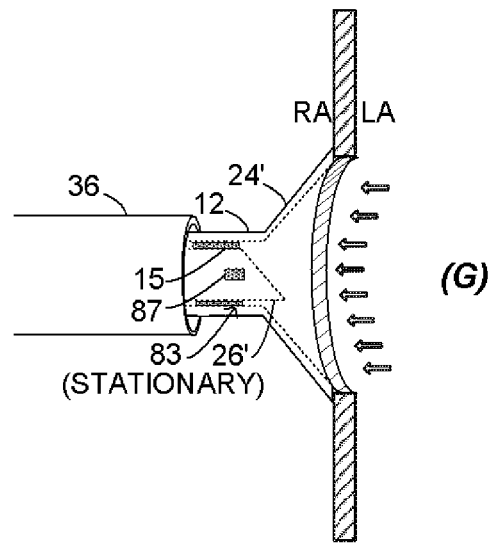
FIG. 8 illustrates a side schematic view of another transseptal access system according to an implementation of the present invention.

In another implementation, shown in FIG. 8, a portion of a needle 26' may be embedded into a semi-flexible tubular element similar to a dilator 83 (similarly seen in FIG. 3 as dilator 83'). In this implementation, a portion of a long needle, which may be similar to a BB needle, has a flexible polymer 24' affixed to its distal portion. The distal end portion polymer portion 24' is affixed to the outer curved portion of a needle by bonds 15 and, during use in the body, the portion 24' deploys into a funnel-like shape.

Certain manufacturing details are now described. The needle may also have a proximal end on which is disposed a luer fitting for a syringe. The tapered or funnel-shaped polymer portion affixed to the distal end may incorporate pleats, such as on some balloons, to help impart a fold during insertion and withdrawal of the device. Furthermore, during insertion and withdrawal of the device, the polymer distal portion may extend past the needle tip and, with the pleats, fold around the distal tip of the needle, protecting the needle from skiving the inner surface of the sheath during movement through the sheath while being inserted into the body.

The prolapsed orientation of the funnel 24 during partial retraction into the sheath 36 enables the inner core to perform as a typical dilator. The tapper portion of the dilator used in a similar way to the dilator of a traditional TS sheath sends tactile information to the proximal end of the dilator where the end-user, grasping the proximal end, can feel the dilator and sheet moving along the septum onto the location of the FO. Furthermore, with the funnel 24 partially extending from the distal end of the sheath, this creates a tapered geometry similar to the traditional dilator, enabling the tapered portion to gradually access the puncture site made by the needle 26. The funnel also provides a positive stop for the needle, thereby acting as a safety feature, preventing the through—and—through perforation common to traditional TS access devices.

After insertion and attainment of the target location, the needle is deployed thru the distal tip of the device. The polymer distal portion may then deploy like an inside-out umbrella against the septal tissue. The needle may be located slightly back from the deployed plane of the polymer funnel portion. Then, using a syringe, a vacuum, suction effect, or other negative pressure between the funnel polymer portion and tissue allows the soft flexible polymer portion to flatten out, pulling the septal tissue inward toward the needle and piercing the septal wall for access to the LA.

Aspects of certain implementations follow.

In some implementations, the funnel is flexible and can flatten substantially perpendicularly to the axis of the lumen of the catheter shaft. In some implementations, when the distal end is flattened against the septum, exposing the tip of the needle-like element, the same extends at least 1 mm past the planar surface of the flattened portion of the funnel-shaped distal end. The funnel may be mechanically capable of flattening by advancing the catheter forward or by creating a negative pressure with the use of a syringe. The needle element may employ a tapper, the tapper being sharp enough to penetrate cardiac tissue. The funnel-shaped distal segment may have a range of angularity from 90 to 180 degrees. In another implementation, the funnel distal portion could be attached to a needle, a dilator or a sheath. In some implementations, the distal portion of the device may employ a pressure transducer to measure cardiac pressure and pressure changes, to define when TS access is achieved. In some implementations, a device is provided such that the distal portion of the device employs an ultrasound element 87 capable of visualizing TS access locations prior to puncture of the FO.

In some implementations, a device is provided where the needle-like element is attached to a tubular element that is advanced distally or proximally by the use of a knob located at the handle of the device. In some implementations, a device is provided having a flexible distal portion to enable steering via a mechanical mechanism 85 located at the handle of the device. In some implementations, a device is provided having a proximal end that includes a handle element having a mechanical slide connected to a tubular structure and a needle or piercing element located at the distal tip, enabling movement in a distal and proximal direction. A proximal end may have a handle that includes a haemostatic valve (e.g., a Merit Medical Passage hemostasis valve (pin 500066)) for guidewire insertion and a luer port (e.g., a Qosina Male Touhy Borst (pin 60343)) to connect a syringe. The hemostasis valve enables insertion of a guidewire or other device and prevents blood from exiting the handle. The sheath portion of the device may employ a fixed curve or may be configured to enable deflection via a steering mechanism 85 at or adjacent to the handle. In this way, the device may be more conveniently directed to a particular location. Where the device employs a fixed curve, a number of difference radii of curvature devices may be provided for use.

In some implementations, a device is provided that, following access to the LA, can be used to deliver contrast to the LA via a syringe through a luer fitting situated on the proximal end of the device, for the purposes of performing venograms.

In some implementations, the cutting element may be slightly off axis and may extend past the surface defined by the lip. In some implementations, a governor 81 or other means may be implemented to inhibit movement of the cutting element past a pre-specified point. In this way, a significant safety factor is added. The mechanism that pushes the needle may be similar to those used to extend the point of a ball point pen (and to retract the same as well).

The elongated member may be a modified dilator. The cone may be fabricated from Sorta-Clear 40A silicone, and may be bonded to the modified dilator using a bond with RTV.

As noted above, variations may be seen especially in the features of the funnel. For example, the funnel may be folded by collapsing in steps, as caused by ribs, so as to allow for easier folding. The wall of the funnel may have a relatively constant thickness, or may have a varying thickness. It has been found that particularly good results are obtained where the wall thickness incorporates a taper, e.g., becomes thinner in the distal direction. In the manufacturing implementations of the invention, a catheter section may be bonded to a cylindrical section mounted to the funnel.

Other variations of the invention will also be seen. For example, the piercing or puncturing or penetrating element may incorporate various shapes of needles, or the same may incorporate RF, resistive, or inductive heating, so as to "burn" a hole in the septum in a convenient fashion. Where a negative pressure is pulled through a hole in the needle, the same may be pulled from the side of the needle or from the tip. Where the negative pressure is pulled from the tip, depending on the diameter of the needle, some septal tissue may be pulled into the needle. In most cases, however, a hole will still be caused in the septum using this technique.

Figure 9:
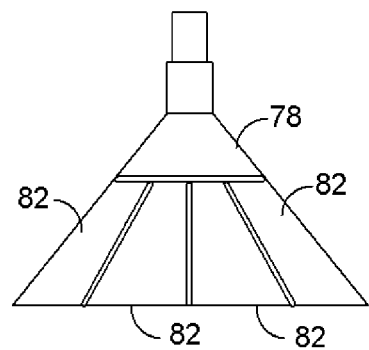
FIG. 9 illustrates a view of a funnel including a partial funnel with multiple segments.

Yet other variations of these designs will also be seen. For example, in some cases it has been found both sufficient and efficient to replace a full funnel with one in which a partial funnel 78 (see FIG. 9) extends partway distally while multiple segments extend distally from the partial funnel to the distal end. In a specific implementation, eight such "fingers" extend from the partial funnel to the distal end, similar to the tentacles of an octopus. This embodiment has the advantage that the same is easy to fold for insertion (as less folding is required), while still being capable of forming a sufficient negative pressure to pull the septum towards the needle and vice-versa. In this connection it is noted that one negative pressure that has been found sufficient is that drawn by retraction of a syringe, e.g., in the range of 10 to 20 cc. In this or in other implementations, the funnel may be deployed by having the same heat shape set, e.g., with a memory alloy having an AF temperature range of 10 to 25° C. And as mentioned before, the guidewire can allow for multiple deployments of treatment devices following the septal puncture. Treatment devices may even be loaded in a cartridge system for multiple easy deployments, where the cartridge system may be mated to the guidewire. Other inventions will also be apparent to one of ordinary skill in the art, given this teaching. Certain other variations are described below, and others will be apparent to one of ordinary skill in the art.

In certain implementations, transseptal access devices and procedures according to present principles are designed to reduce the stress induced into the tissue (FO) to minimize and reduce fibrosis from scarring said target tissue location over currently available and marketed TS access devices. They generally overcome this without the need for RF being delivered to the needle. The devices enable a novel use of vacuum or negative or low pressure to hold and or encourage the tissue towards the needle while the physician through the use of a knob located on the proximal end, i.e. handle, advances a needle forward (if necessary) to puncture the tissue. This device overcomes the limitations of the conventional and RF TS access devices by using the vacuum to enable the device to maintain position, and pull the tissue into the cone thinning the tissue and enabling the needle to simply and safely penetrate the tissue with a minimal amount of force required by the end user. Additionally, this simple change in the methods eliminates the sudden release of tension by said tissue that causes perforations known to conventional TS access devices. Moreover, ultrasound or RF energy may also be added to activate the needle for very difficult and thickened septal tissue. The device described may have alternative uses in addition to TS access such as used within a vessel that is full or partially occluded. The device maybe deployed into said vessel encounter said blockage, deploy the distal segment the cone maybe used to center said device within said vessel and the needle advanced thru the blockage, lastly a guidewire may than be advanced thru lumen of said needle to pass thru and dilate a lesion within said vessel lumen. Furthermore, the needle of the proposed device may also enable the conductance and delivery of an energy source such as ultrasound or RF energy to reduce the amount of force required to penetrate and open a blocked or partially blocked vessel.

Figure 10:
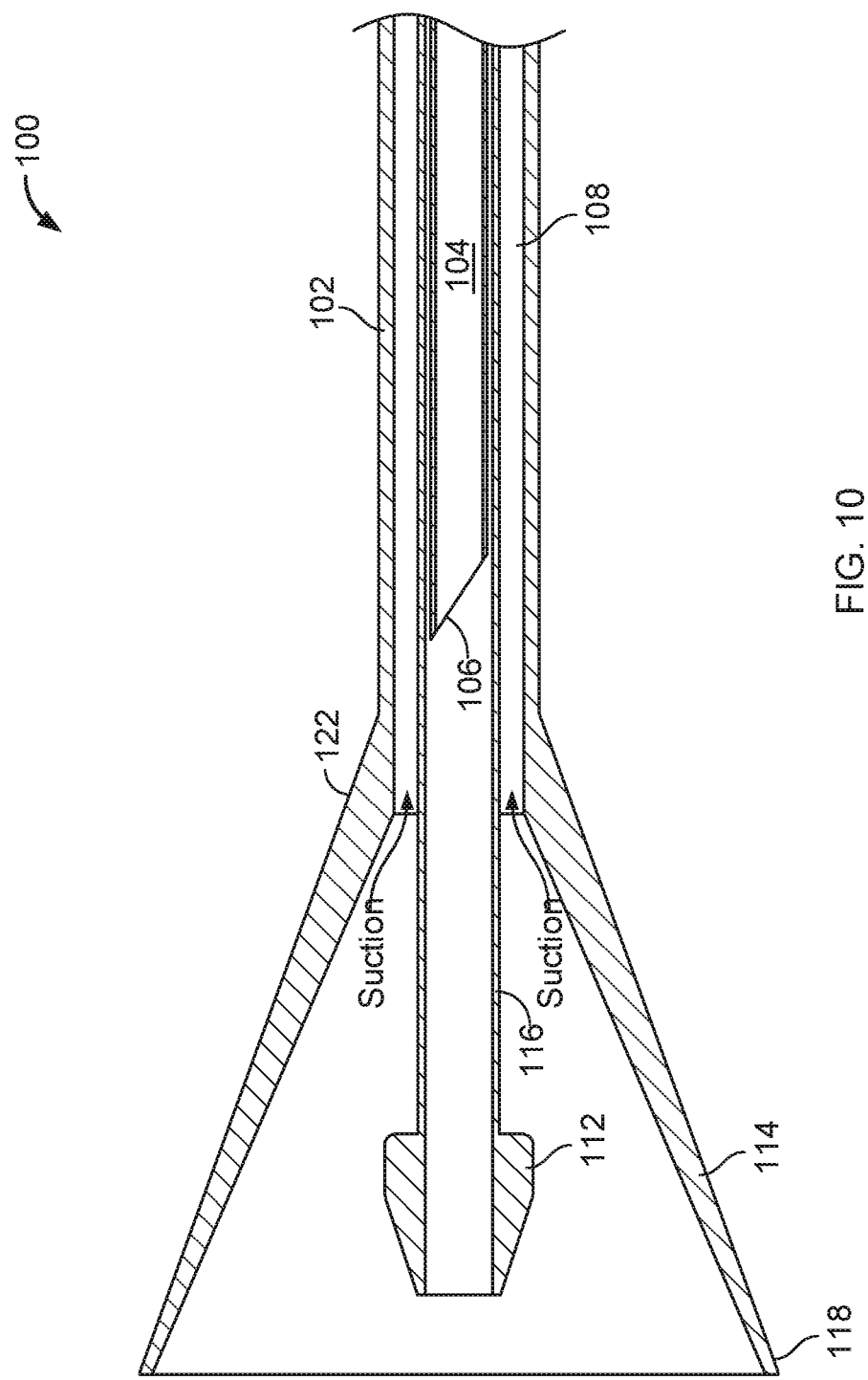
FIG. 10 illustrates a side sectional view of a device according to present principles

In one implementation, depicted in various illustrations in the figures, such as in FIG. 10, the needle 106 that provides a puncture may be actuated axially (distal and proximal), i.e., may be caused to move, rather than being stationary as is described in most implementations above. FIG. 10 shows a side sectional view of such an implementation, in which the needle six is situated at the end of an elongated member 104 which moves within a needle sheath 116. At a distal end of the needle sheath 116 is an element 112 which may be employed to assist deployment of the funnel 114, having a proximal end 122 and a distal end 118. An introducer sheath 102 supports the funnel 114. Suction is provided along a lumen 108.

Figure 11A:
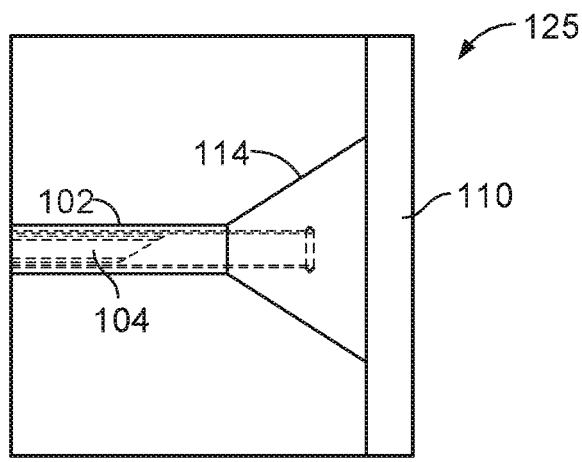
FIGS. 11A-11C illustrate steps in deployment of a device according to present principles.
Figure 11B:
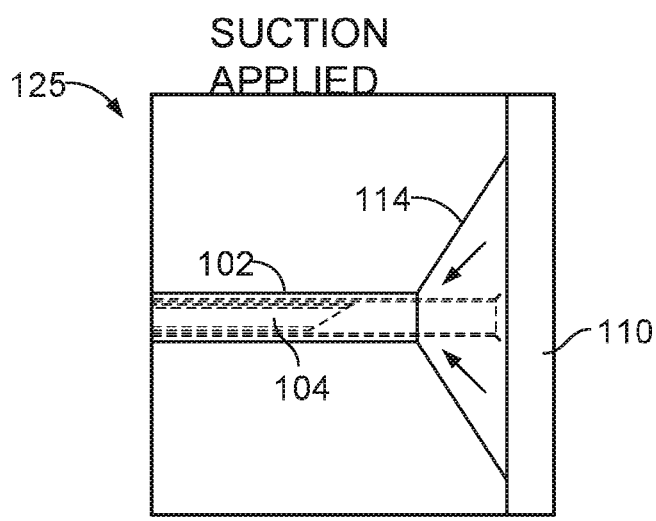
Figure 11C:
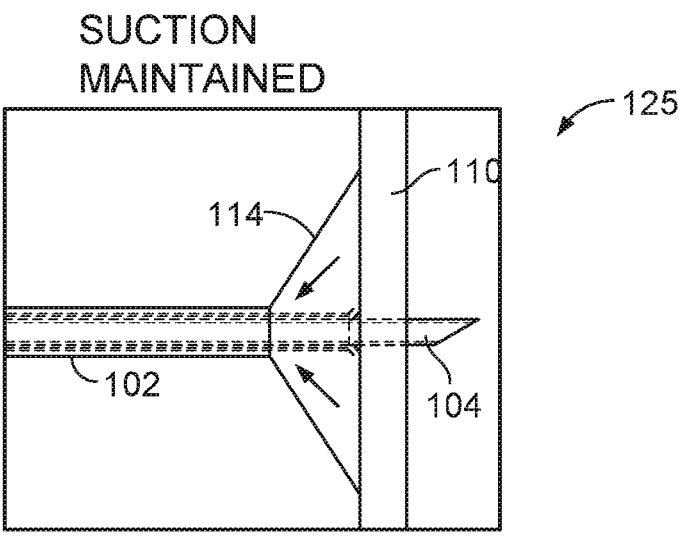

FIGS. 11A-11C depict the distal end of the device and its interaction with the septal wall 110 during use. FIG. 11A shows the initial engagement of the funnel 114 with the wall. Slight forward pressure against the wall, or application of initial vacuum, may result in partial collapse or prolapse of the funnel which eventually brings the needle sheath lumen in contact with the wall, as shown in FIG. 11B. Alternatively, the needle sheath 102 may be manually actuated to this point of contact. In either case, two separate seals are formed against the wall, and suction may then be isolated to the region between. When the needle 104 with tip 106 is advanced, it may puncture the wall and access the adjacent space without compromising the suction, as shown in FIG. 11C and further explained below.

The actuation or movement may be employed by use of a knob on the handle forming the proximal end of the catheter. The same may be a short needle coupled to the distal end of the device, and may be, e.g., connected to a reinforced polymeric lumen to transmit forces such as the push and pull needed for puncture. The needle may be actuated within the needle sheath, and the needle sheath may also isolate the suction to outside the needle and the sheath. In this way, once penetration has been made through the tissue, the negative pressure is maintained, rather than being relieved by an in-rush of fluid such as blood into the body of the catheter, and in particular, into the lumen from which negative or low pressure was pulled. In some implementations, the needle sheath may be also be allowed to actuate axially (distal and proximal) within the funnel shaft. In other implementations, the needle sheath may be fixed to one position, to simplify procedural use of the device. In either case, the needle sheath serves house the needle and to isolate suction to the space between its outer surface and the inner surface of the funnel and funnel shaft.

Figure 12:
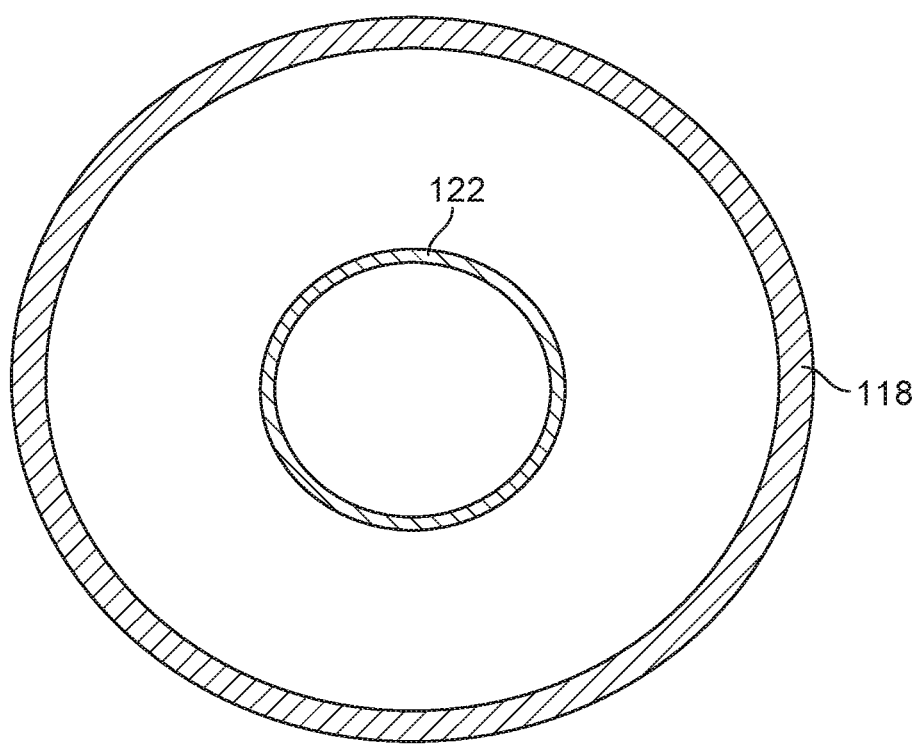
FIG. 12 illustrates a sectional view of a device according to present principles.
Figure 14A:
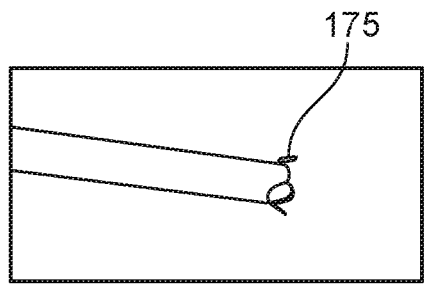
FIGS. 14A-14D illustrates a variation of a device according to present principles.
Figure 14B:
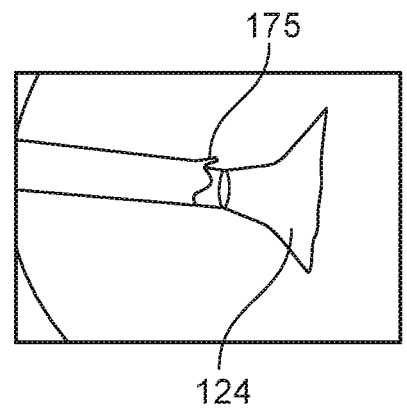
Figure 14C:
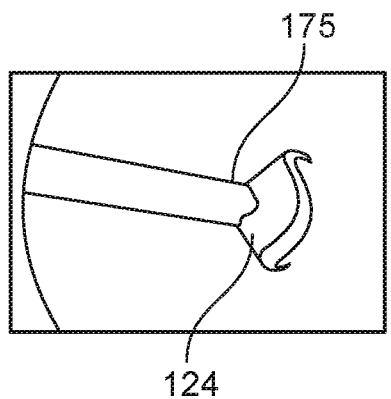
Figure 14D:
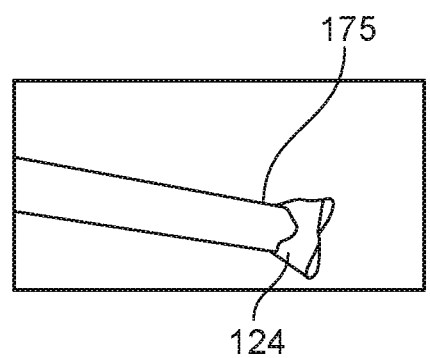

FIG. 12 below depicts the key areas of the septal wall that are affected during the use of the device and this isolation of suction or negative pressure. The distal edge of the funnel initially contacts and makes a seal with the septal wall in the area indicated 118. The distal edge of the needle sheath contacts and makes a seal with the wall in the area indicated 122. When negative pressure is applied to the device, this negative pressure is localized to the volume between elements 118 and 122, which is outside of, and isolated from, the area of needle puncture (inside of element 122). In this way, the negative pressure in the volume between elements 118 and 122, and the position of the device against the septal wall, is maintained during needle advancement, puncture, and penetration into the adjacent cavity (ie: the left atrium in a transseptal access procedure).

The needle sheath may also have a soft polymeric tip (ie: low durometer PEBAX or silicone) to enhance the seal against the septal wall. In implementations where the needle sheath is allowed to actuate within the funnel shaft, the tip of the needle sheath may also be used subsequent to the needle puncture, to dilate the hole in the tissue formed by the needle. In the implementation shown in FIG. 10 above, the tip of the needle sheath is shown as a large tapered tip to enhance this dilation.

A proximal handle may be employed which incorporates a syringe like device to form a low pressure along the distal segment or within the cone of the device. The handle also allows user control over the extension of the needle, e.g., how far the needle is allowed to move or actuate. Movement increments may be provided by an appropriate mechanism, as well as stops and locks to control over extension.

In a related implementation, and referring to FIGS. 13A-13F, where the device is delivered through an introducer sheath or guiding catheter, the combination may be configured such that a slight pullback in the sheath deploys the funnel or cone. As may be seen, the septal wall 110, and in particular the fossa ovalis, may be punctured and penetrated in various steps as shown, including deployment of the funnel 114 allowing suction and puncture by the needle 104. The funnel or cone is preformed but during delivery is constrained to be within the delivery sheath. Once outside the sheath, the funnel or cone adopts its preformed shape for affixation to tissue. Forward pressure of the funnel creates the seal against the tissue. A vacuum or other low pressure (or negative relative pressure) may then be applied, and the tissue may be either pulled across the needle or the needle gently extended through the tissue, or a combination. In either case, over extension of the needle and deleterious consequences to nearby tissues is avoided. It is noted that even if the suction cup is not directly touching the tissue, once suction is applied, tissue still gets pulled into the cup, allowing sufficient contact for negative pressure to be drawn and maintained.

The benefits of implementations that provide isolated suction include the maintenance of suction, equivalent to maintenance of position, before, during, and after puncture. Users are also offered additional control over the depth of needle puncture and/or access. The needle may be hidden or withdrawn (or removed completely during delivery), mitigating risk to the funnel from damage due to the needle tip, and mitigating a stiff needle's affect on system flexibility.

Referring to FIGS. 14A-14D, having features 175 in the inner diameter of the sheath may cause an improved ability to fold the funnel 124 into the sheath. For example, referring to the figure below, improved folding may be caused by having periodic features such as invaginations in the interior of the distal end of the sheath.

Figure 15:
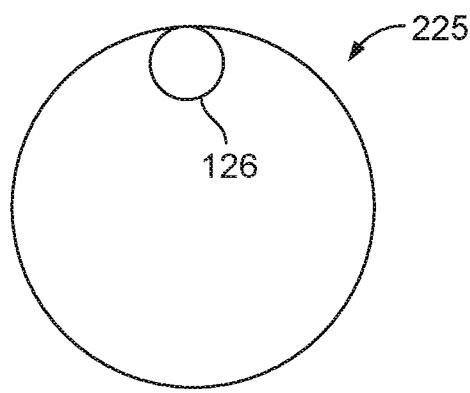
FIG. 15 illustrates a sectional view of a device according to present principles.

In FIGS. 14A-14D, a sinusoidal or periodic invagination with four features. But, referring to FIG. 15, even a single discontinuity 126 in the inner diameter 225 of the sheath can lead to enhanced folding. This discontinuity may be implemented by a single rib or spline, which as noted creates a buckle point or collapse point for the funnel. A benefit of such implementations is that the same allows for a full conical shape for the funnel, for optimum suction during use.

Figure 16A:
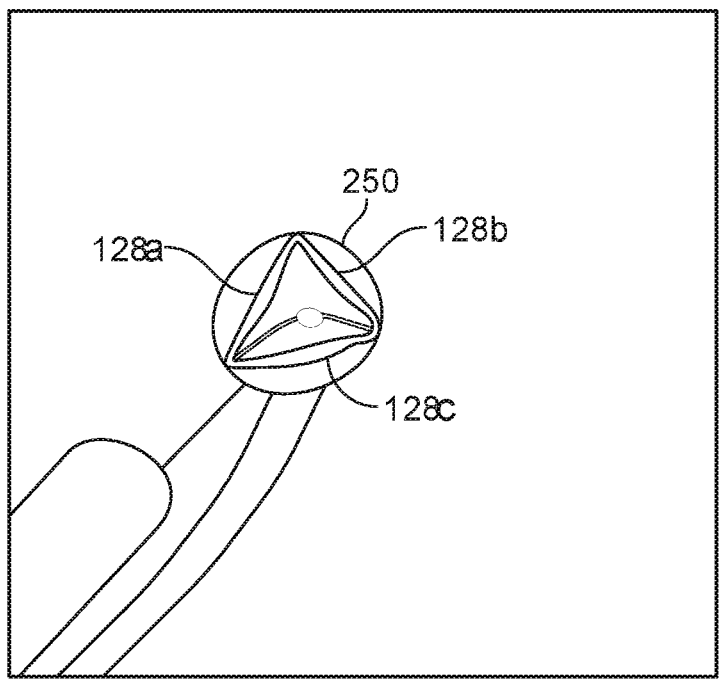
FIGS. 16A-16B illustrates a variation of a device according to present principles.
Figure 16B:
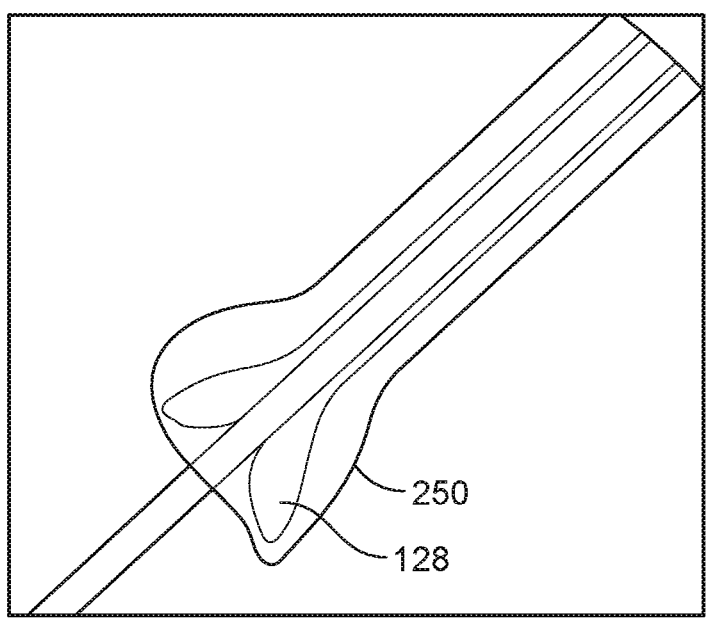

In another implementation, as shown in FIGS. 16A-16B, a funnel 250 may be made inflatable, i.e., may be made out of a balloon, e.g., one that is folded back on itself. In the figure, the funnel is thus made of a balloon that has formed three segments 128a, 128b, and 128c. By causing the funnel to take its deployed shape via inflation, the funnel may be made very stiff during suction but very collapsible during delivery and retraction. As an example, an inverted 4.0 urethane balloon was tested with good results. Suction was successfully obtained and maintained.

Figure 17:
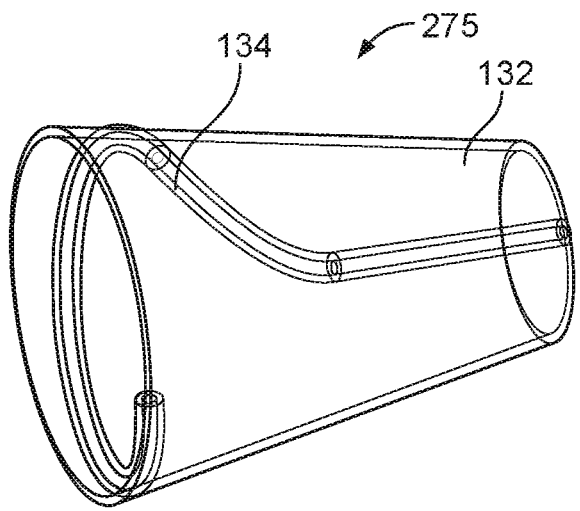
FIGS. 17-30B illustrate variations of types of funnels.

In another implementation, shown in FIG. 17, a device 275 may include a funnel 132 in which the funnel is reinforced with, e.g., a nitinol coil 134.

The nitinol coil reinforcing member provides additional radial strength to the funnel, and can be retracted into the catheter prior to the collapse of the funnel, allowing the funnel to easily collapse to a small profile. The nitinol wire component may be attached to the needle sheath and advanced forward prior to creation of the vacuum to support the cone from collapse during application of said vacuum or delivered in a straight configuration, constrained by a straight delivery lumen, but upon deployment of the funnel, may be delivered into a coiled polymeric tube that is molded as part of the funnel, allowing the coil to adopt its preformed shape. The nitinol wire may be pre-shaped as a coil, e.g., as noted in the figure, and may adopt that configuration upon release from the straight lumen in the delivery sheath or catheter. In this way, the funnel's suction stiffness is decoupled from its collapse stiffness.

Figure 18:
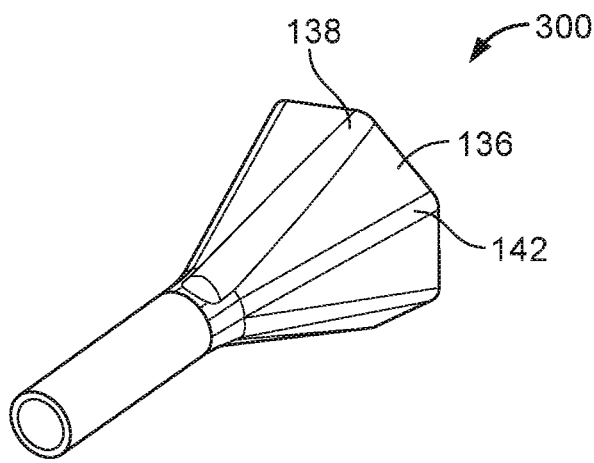
Figure 19:
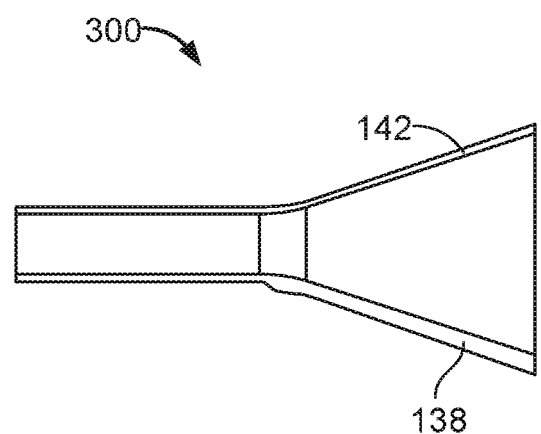
Figure 20:
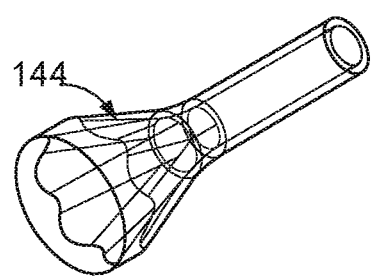
Figure 21:
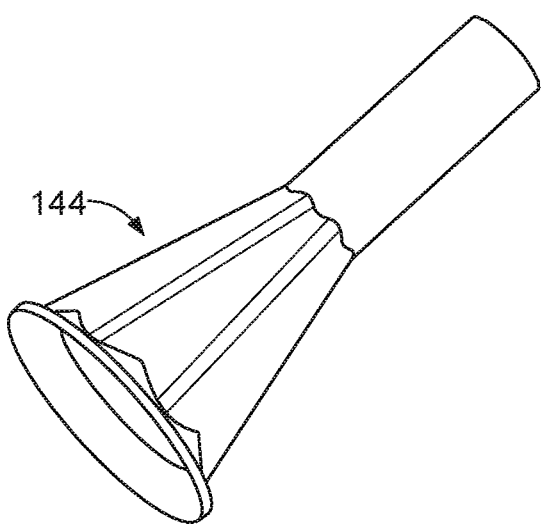
Figure 22:
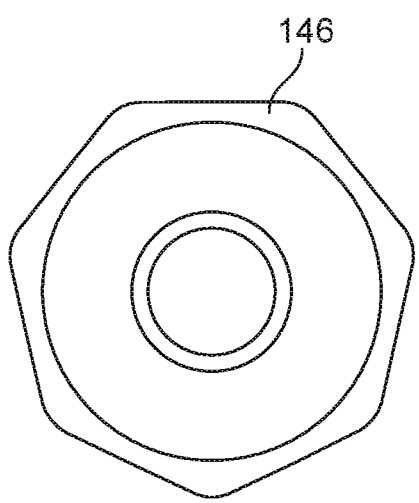
Figure 23:
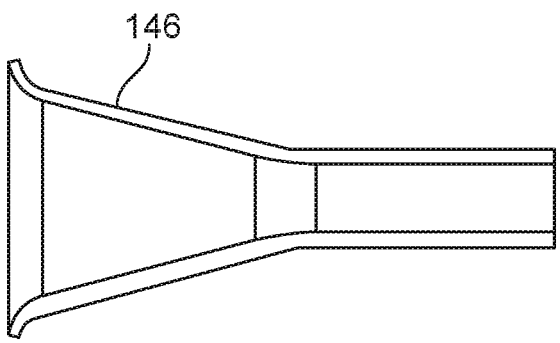

As illustrated in FIGS. 18 and 19, a device 300 may include a funnel or cone 136 which may be implemented with a polygonal outer and/or inner shape. Such may in some implementations create a variable thickness around the circumference of said cone, and may advantageously create "automatic" or inherent loci for collapsing, e.g., "collapse points". Significant collapsability has also been discovered with funnels having just a single rib or spline on their surface, as the same creates anisotropy in folding, and thus induces a crease or other fold to happen. Different size ribs 138 and 142 may be provided to further create anisotropy for folding.

In an alternative implementation, the outer surface of the funnel or cone may have a particular shape, e.g., be heptagonal (or other shape), while the inner surface of the funnel or cone may have a different polygonal shape, which may be of lesser order than the outer surface, e.g., pentagonal, etc. Such adds flexibility to the funnel and provides internal features to add support to the same, e.g., in a similar manner as ribs. Additionally, the heptagonal shape can spiral down the length of the funnel.

Figure 24:
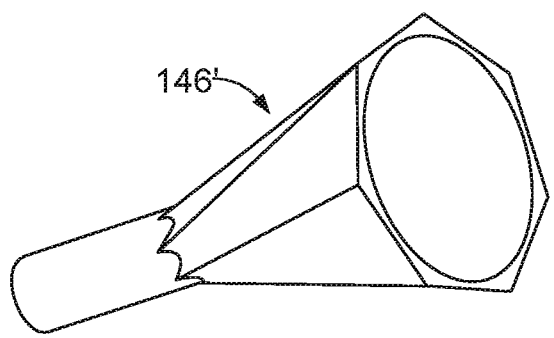
Figure 25:
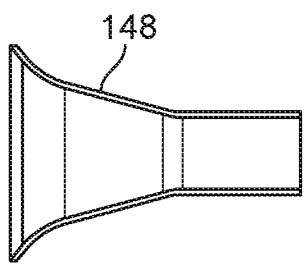
Figure 26:
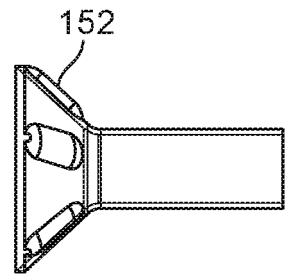
Figure 27:
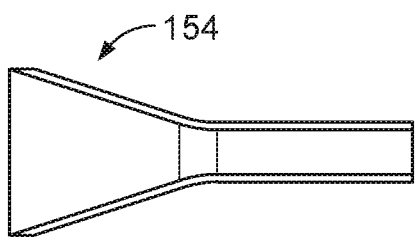
Figure 28:
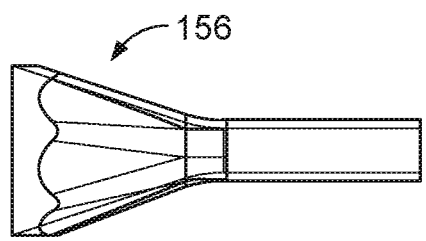

FIGS. 20-30B illustrate various other varieties of finals, including a ribbed funnel 144 with a circular opening (FIGS. 20 and 21), a heptagonal funnel 146 (FIGS. 22 and 23), and a spiraling heptagonal funnel 146' (FIG. 24).

Figure 29:
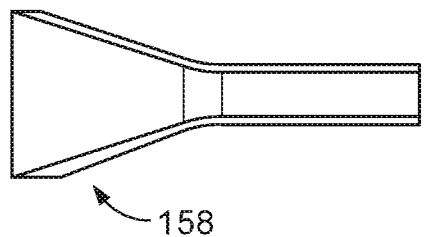

A variety of other funnel types may be employed to improve the collapsed profile, apposition and sealing to various tissue surfaces, and/or the radial strength when deployed, and certain of these are illustrated in the figures. These include a segmented funnel 148 (FIG. 25), a ribbed funnel 152 (FIG. 26), a straight funnel 154 (FIG. 27), a straight ribbed funnel 156 with a fluted distal end (FIG. 28), and a funnel 158 having a nonuniform thickness (FIG. 29).

Variations of the systems and methods may include one or more of the following.

In one variation, the cone or funnel portion of the device may be, in lieu of a solid cone, constituted of overlapping pleats, like flower petals. The petals may overlap so that the application of the vacuum or negative pressure causes the same to appropriately seal to the tissue to allow the tissue to be pulled towards the needle. The pleats may be formed before or after a molding procedure of the funnel. The pleats may be connected, such as in articles of clothing, or made be disconnected, such as like flower petals. In any case, the pleats allow convenient folding and unfolding, e.g., retraction and deployment, of the funnel.

The funnel may be configured to be self-expanding or may be caused to expand such as, e.g., by the nitinol wire described above. The entirety of the interior of the funnel may be caused to be a low or negative pressure volume, or as noted above a central lumen (through which the needle or other penetrating element is delivered) may define a volume which is not subject to low pressure.

The funnel may be injection molded, such as a molded PEBAX funnel, which then allows melt-flow bonding to the shaft of the catheter. The funnel may employ a variable wall thickness, which allows the stiffness to transition from the portion of the funnel attached to the delivery device to the portion at a distal end. In the same way, the funnel shape itself may transition from a proximal end to a distal end, as shown in the figure below, to assist the ability of the funnel to properly seat and seal against tissue, e.g., by making the distal end more flexible.

The funnel may be made radio opaque, e.g., with embedded wires, e.g., platinum or the like. Alternatively, instead of embedded wires, the funnel may be heat bonded with radio opaque polymer tubes. In yet another implementation, the cup material itself may be compounded with radio opaque materials such as tungsten, barium, or the like. The radio opaque features may have specific geometries to assist the physician in visualization of the orientation of the system under fluoroscopy.

The funnel may be made flexible or articulating, the neck of the funnel or cone may also include bellows or have a bellows-like design similar to a strain relief to enable the neck of the funnel or cone to have increased flexibility so as to be able to create a strong enough seal to allow the funnel to hold against a surface that is not perpendicular to the axis of the catheter.

As in the polygonal funnel structures described above, the funnel may include one or more elements to impart a forced or assisted folding of the funnel or cone during retraction of the funnel into the delivery system. The funnel may be formed to have a "memory", such that during retraction and extraction, the same transforms from a collapsed to a deployed configuration (and vice versa) in a consistent manner.

The funnel may further be provided with a plurality of electrodes along its distal end, e.g., the edge of the funnel that contacts the tissue, which may then be employed to enable mapping to be used to identify the FO for proper location to make a puncture.

The funnel may also be provided with a series of needles positioned along the edge or rim, e.g., the distal end, to enable longer-term fixation of the funnel to the tissue. The needles may also be employed to hold the device for procedures such as a closing of the incision made by the main or central tissue-penetrating element, e.g., for procedures such as open-heart procedures for valve repair or replacement. In this application, once access to the heart is made to the chest, a device according to the present principles may be advanced to the exterior surface of the heart. Low pressure may be applied as discussed to seal the device to the heart. The exterior needles arranged around the circumference of the funnel may then pierce the heart in addition to the vacuum to hold the position for longer procedures. The needles may further be provided with a suture mechanism to suture the device to the tissue. At the end of the procedure, the ends of the suture may be pulled and the access point closed.

The vacuum may be caused by a syringe attached to the handle or incorporated within the handle which is in pressure communication with the lumen at a proximal end of the catheter, the lumen being in pressure communication with an interior of the funnel at a distal end. Pulling back on a plunger of the syringe changes the shape of the tissue via the pressure communication, and the change of shape may be convex or concave, depending on the shape of the funnel, such that the tissue is biased towards the tissue-penetrating element such as the needle. A locking syringe (i.e.: Merit Medical VacLok Syringe) may be useful to maintain the negative pressure for extended periods of time during the procedure. In some implementations, the pressure may be drawn locally, at the distal end of the catheter, rather than remotely by a device such as a user-operated syringe. This element and procedure may also increase tissue/blood perfusion locally that might also benefit the patient depending on clinical use.

The catheter may include more than one lumen, although generally at least one is required for the pressure communication. Other lumens may be employed for the transmission of gases or fluids or a guide wire or other devices such as biopsy needles etc. In the implementation noted above, where the funnel is inflatable, a lumen may be employed to deliver an inflation fluid or gas.

The needle sheath lumen may be spring loaded or adjustable in length to provide optimum opposition to the tissue being penetrated by the needle. Additionally, this lumen can provide a channel for blood to flow from the opposite side of the tisse after the needle has penetrated. This could be used as an indicator that the needle has penetrated or for pressure readings or blood coagulation or viscocity measurements to aid the physician in obtaining and or monitoring in-procedure hemodynamic conditions commonly known as Activated Clotting Time (ACT) measurements.

The tissue-penetrating element may be solid or may have an internal lumen so as to enable passage of a guide wire. The same may also be a lead, biopsy tools such as forceps, or the like. A lumen within the needle or other tissue-penetrating element may be appropriately-sized to allow some of the septal or other tissue to be pulled into the lumen, e.g., for additional fixation, drug delivery, a procedure, a biopsy, or the like. The needle or other tools delivered thru said lumen of this device may also transmit an energy source as a therapeutic agent that include but not limited to RF energy to cauterize, ablate or perform other therapeutic elements.

Systems and methods according to present principles may be applied in other areas of the body i.e. lungs, heart, and external of the heart as well. For example, within the heart, systems and methods may be employed to aid in lead placement for pacemakers. For example, with a funnel appropriately miniaturized, TS access may be achieved and the miniaturized device delivered through the TS sheath to enable a lead to be placed in the atria or ventricles or other organs. The funnel or cone may be advanced to the area of interest in the atria or ventricles and the syringe or other device used to cause a low-pressure volume to be created, affixing the funnel to the tissue site. By using a different lumen, e.g., a working lumen, a lead can be advanced and may penetrate the tissue or by using the lumen of the needle of the device, e.g., by passing the lead through the lumen of the tissue-penetrating element, and into the tissue for ICD procedures. Other lumens may also be employed. A reverse procedure may be employed for lead extraction.

Exterior of the heart, systems and methods according to present principles may be employed in a number of indications, including in endoscopy, gynecology, laparoscopy, other surgical procedures, and generally any procedure involving passage through a tissue. Systems and methods according to present principles may be employed to directly access tissue or organs for minimally-invasive procedures without the need to use the body's vascular system. The systems and methods according to present principles may be employed to hold tissue by the maintenance of the suction, yet subsequently have a separate lumen employed to enable physicians to directly access the tissue or adjacent tissues, e.g., organs, for biopsy, ablation, etc.

Following TS access, a guide wire may be advanced and the sheath, e.g., an SL1 (8F sheath) may be exchanged for a 12 to 14 French sheath or other device.

Instead of the needle, a tip ablation electrode may be advanced to provide and perform ablation while the suction cup holds the position. The suction cup can also draw cooled saline over the tip to cool the electrode, and moreover the suction cup may prevent emboli from floating in the left atrium, improving the safety profile for ablation. In other implementations, other cone shapes besides a round: shape may also be employed. For example, the outer geometric shape may have a number of sides while the inner shape may have one or more less sides to form variations of cone thickness along the length of the cone to improve resistance to compression under vacuum and allow the points of the cone to provide "rib" like features for stability and controlled collapse of the cone during introduction and withdrawal from the sheath or guide catheter.

Figure 30A:
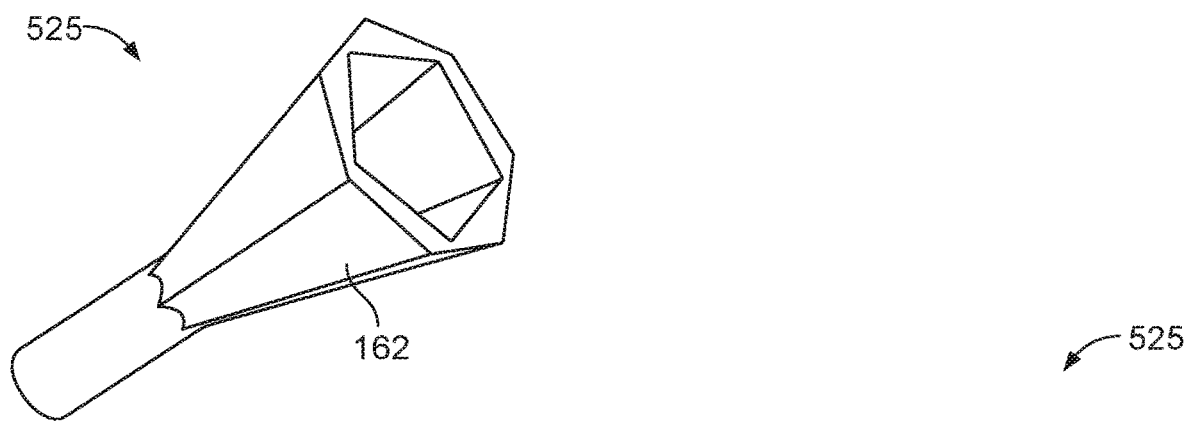
Figure 30B:
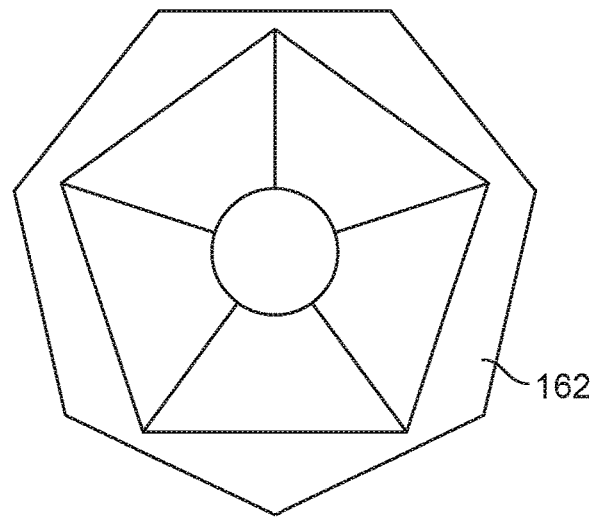
Figure 31:
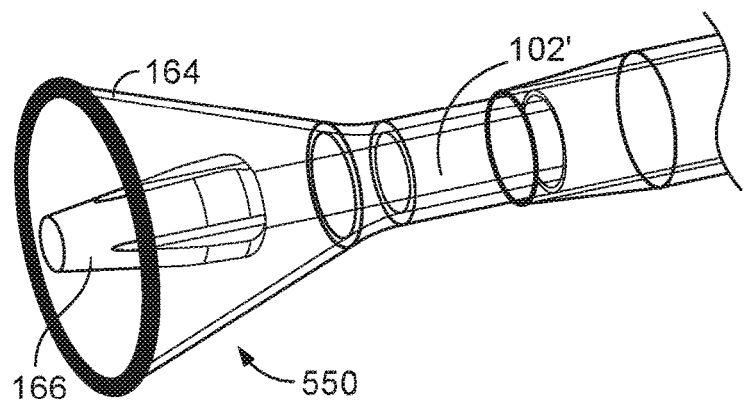
FIGS. 31-39 illustrate variations of types of funnels including a "bullet" element configured to assist funnel deployment.
Figure 32:
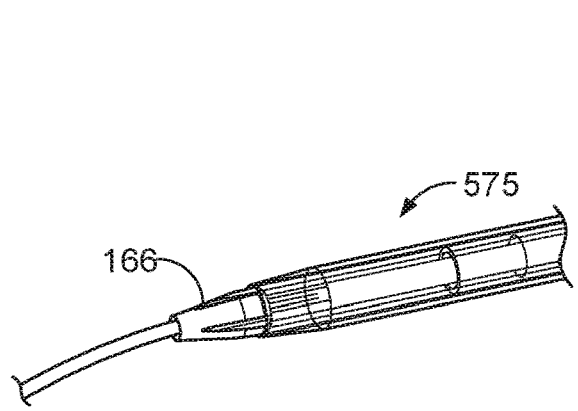
Figure 33:
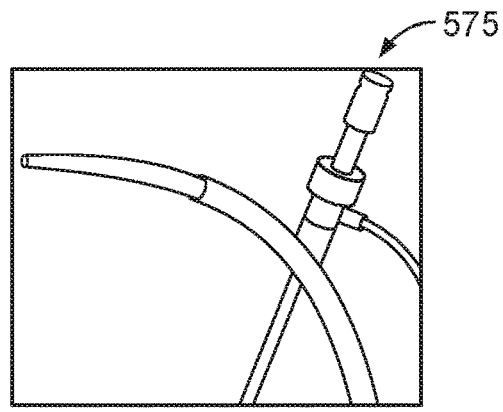

FIGS. 30A and 30B indicate in oblique and end views an example 525 of such a cone shape 162.

In yet another implementation, shown in FIGS. 31-39, termed a "bullet tip" implementation, a device 550 according to present principles includes a bullet tip shape 166 which is used to enhance expansion and/or deployment of the funnel/cone 164, or suction cup. This implementation may also take advantage of an introducer tool, and may also employ various slitting mechanisms as alternatives to dilation. The slitting mechanisms may use a reverse cutting technique or tool. Moreover, an inverted funnel may be employed in conjunction with the bullet tip.

In particular, and referring to the figure below, a device according to present principles 575 may include a needle sheath component 102' having in one portion a shape of a bullet tip 166 (also just termed a bullet tip) may be employed at the distal tip of the sheath 102' and within the funnel 164. The bullet shape, in particular at its proximal end, serves in part to initiate funnel expansion in a conical shape due to its flared nature.

The bullet tip has a shape similar to that of a traditional dilator, especially when retracted to abut the remainder of the sheath, as described below. Various views are shown in the figures.

Figure 34A:
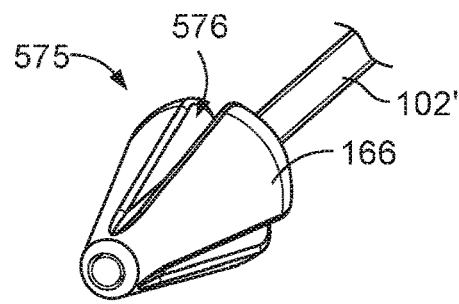
Figure 34B:
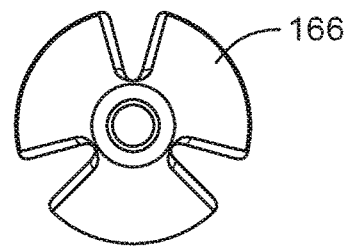
Figure 35:
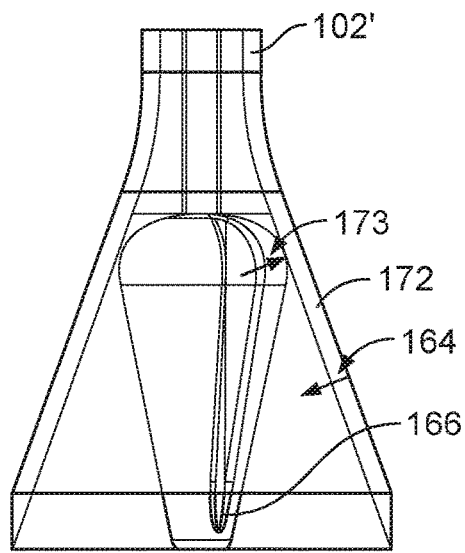

As seen in FIG. 34A, the bullet tip with relief cuts may further have fluid transmission features 576, such as slits, channels, conical shaped slots, or gaps that run from a distal end to a proximal end, and that provide fluid transmission, allowing the improved fluid flow for suction, vacuum, or negative pressure. The conical shaped and slots also allow the suction to be increased by creating additional vorticies. The conical shaped slots may include a single or multiple slots that perform several functions in addition to multiplying the force of vacuum, fluid path, etc.

Other features may include that the bullet tip is radio opaque, so as to allow visualization of the distal tip of the device under fluoroscopy. In another implementation, the tip may have a metallic band encircling a polymer tip, e.g., made from Pt/Ir, etc. The bullet tip may further be formed from a radioopaque compounded polymer.

Following transseptal access via a wire, the bullet tip may assist in dilation, providing a smooth OD transition to the TS sheath, and in this way allows the replacement of the traditional sheath dilator.

As noted above, and referring to FIG. 35, the bullet shape provides internal support to the funnel, especially during suction. It props the funnel open, as shown by the force arrow 173, prevents collapse of the funnel under vacuum, and improves the suction force (see arrow 164). It further has the advantage of allowing thinner funnel walls and a shallower taper angle, providing an important advantage not seen in prior systems.

Figure 36:
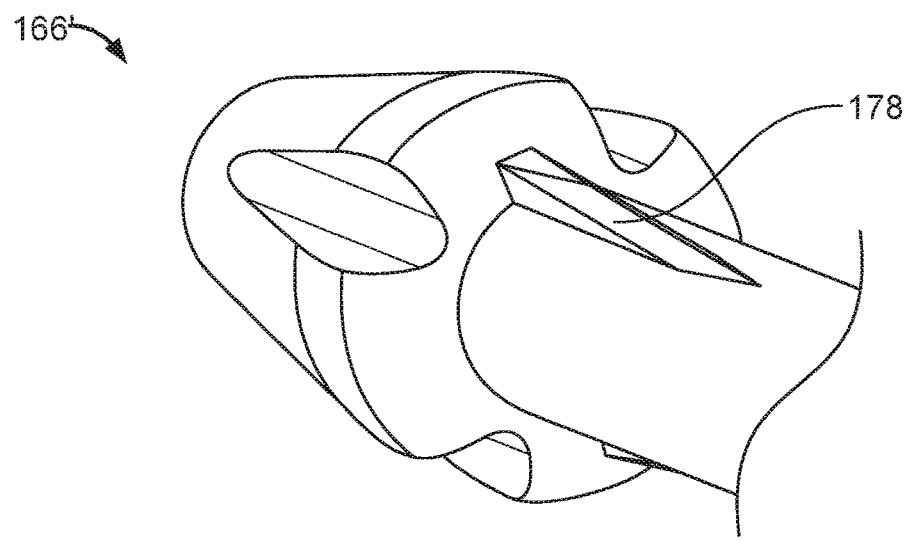
Figure 37:
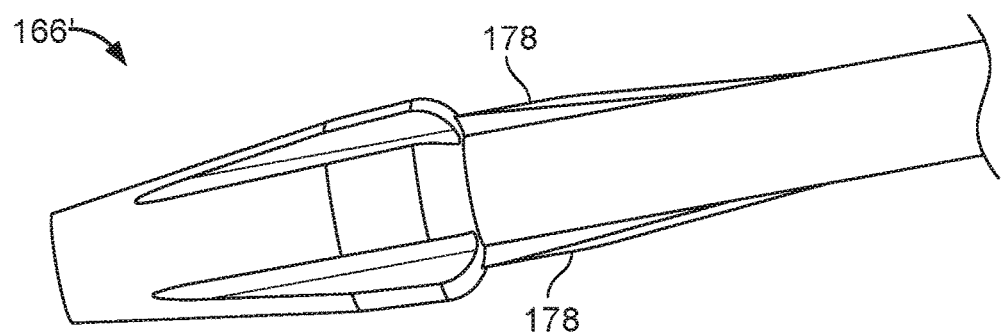

In an enhanced implementation, and referring to FIGS. 36-37, a device 166' includes a referring to FIG. 40 blade 178 disposed on the proximal side of the needle sheath bullet. In this way, the bullet tip is advanced past the fossa ovalis, then the gblades slit the FO upon retraction of the needle sheath back through the FO. While two blades are shown, it will be understood than any number of blades may be employed, including just one.

Figure 38:
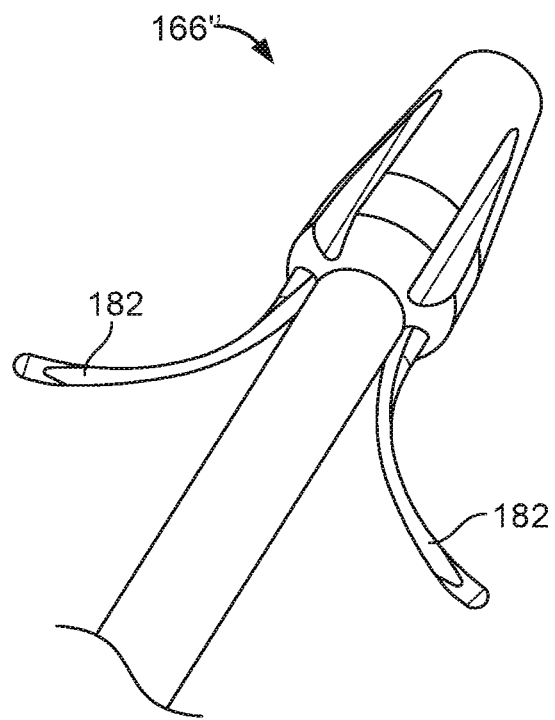
Figure 39:
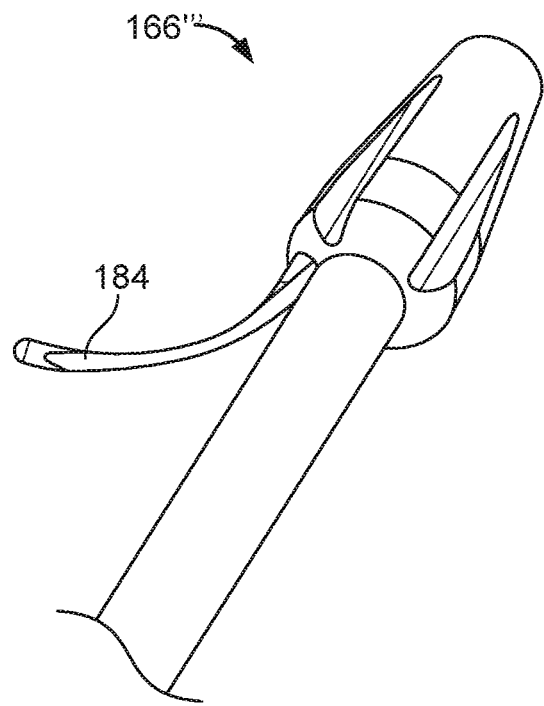

Referring to FIGS. 38-39, a device 166" according to present principles may incorporate another exemplary slitting mechanism in the form of sharpened wires 182 bonded to the needle sheath (not necessarily on the bullet itself). The blades are constrained inside the funnel sheath until the bullet is advanced into the left atrium. Upon advancement, the blades are released into the left atrium. Upon retraction of the needle sheath back through the FO, the blades slit the FO as desired. As a safety feature, only the back side of the wire is sharpened. The blade is thus only exposed when needed to cut the FO. Upon retraction back into the funnel and/or funnel lumen, the blade edges are shielded until the same are safely in the device. In FIG. 39, a device 166''' is shown with just one blade 184 attached.

Figure 40A:
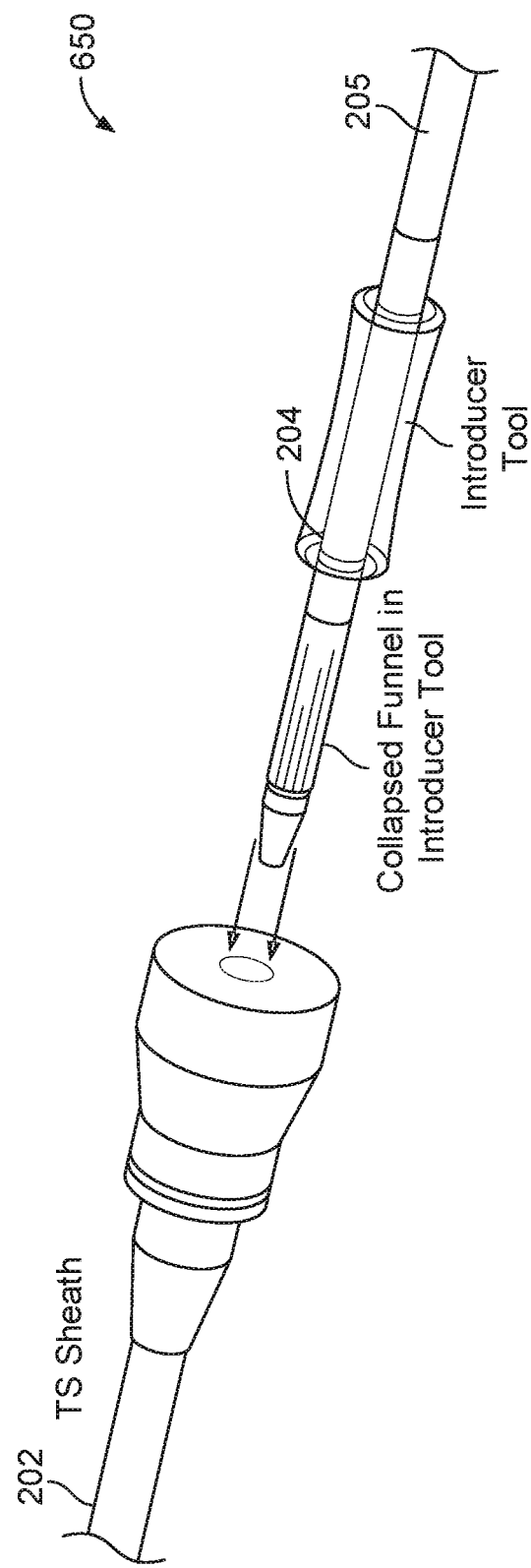
FIGS. 40A-40J illustrate steps in funnel deployment.
Figure 40B:
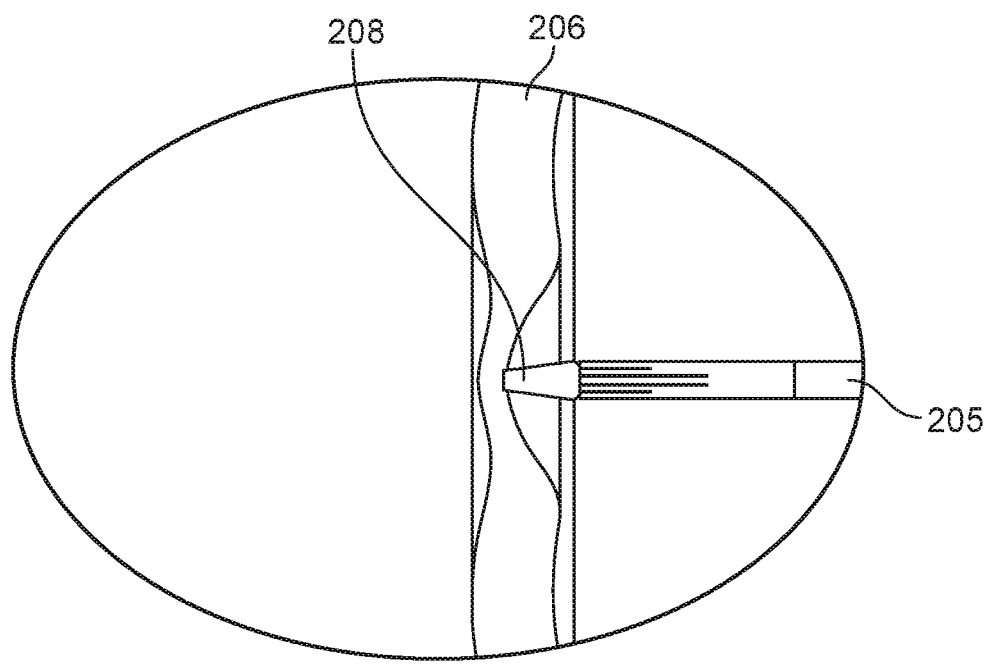
Figure 40C:
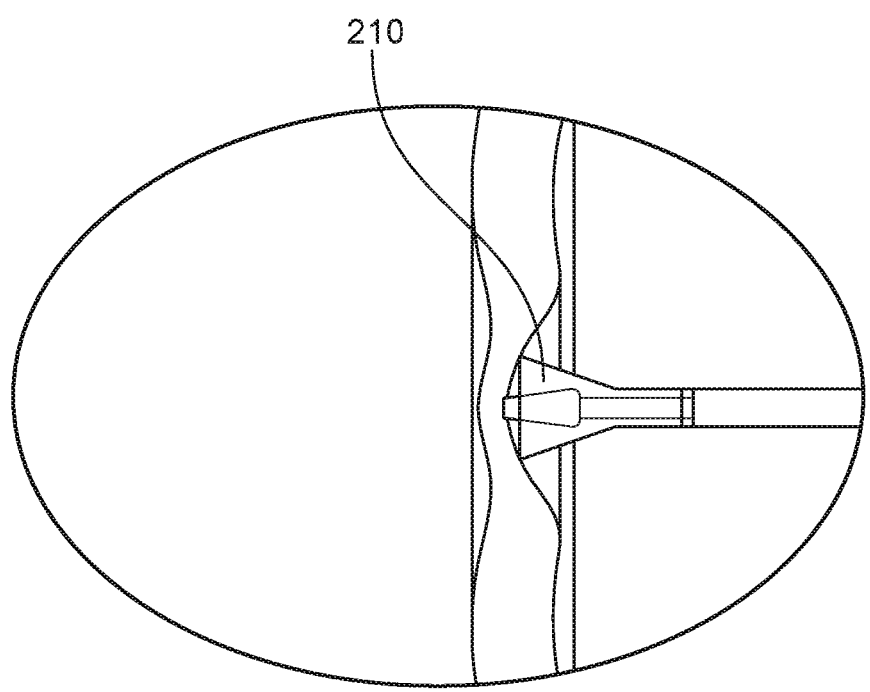
Figure 40D:
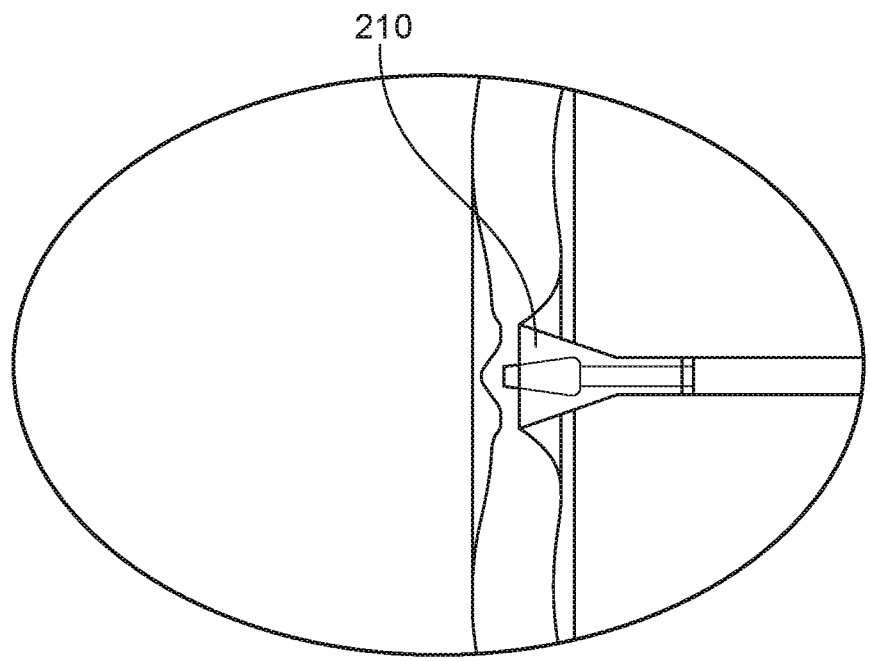

FIGS. 40A-40J illustrate an exemplary method of use. Referring to FIG. 40A, a device 650 includes an introducer sheath 205 having a collapsed funnel within the sheath. An introducer tool 204 may be employed to assist introduction of the device into a transseptal sheath 202. In FIG. 40B, the device having a tip 208 is pushed against the septal wall 206. The funnel 210 deploys in FIG. 40C, e.g., via pullback of the sheat, and suction is activated in FIG. 40D. After suction is applied, the needle moves easily through the FO, or in some cases the suction itself is enough to cause the FO to move past the needle, providing the desired puncture.

Figure 40E:
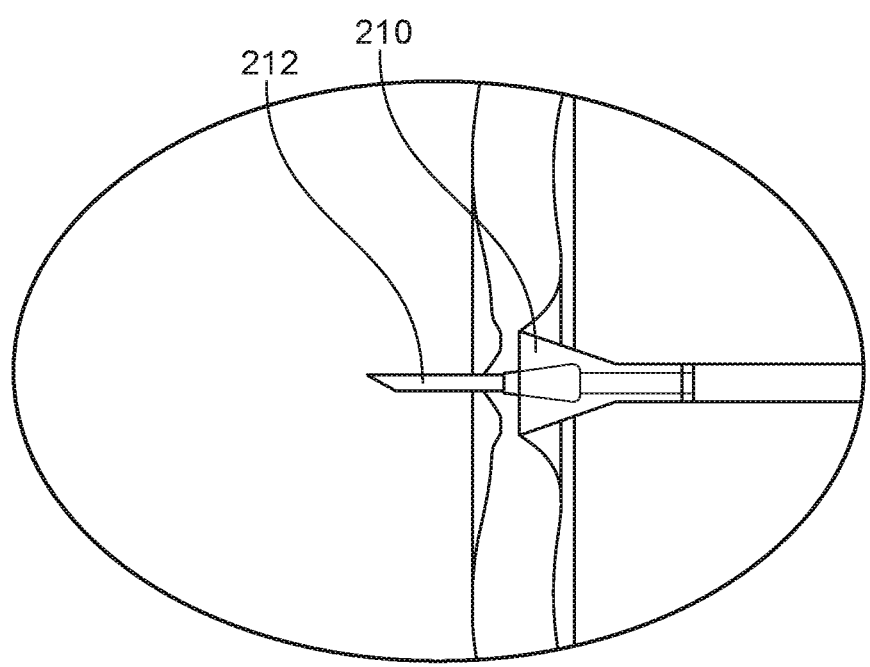
Figure 40F:
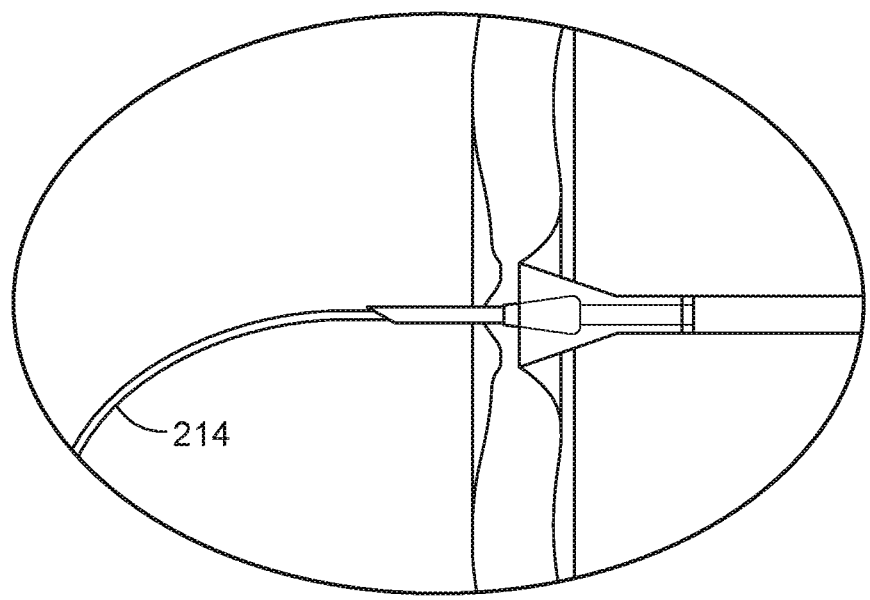
Figure 40G:
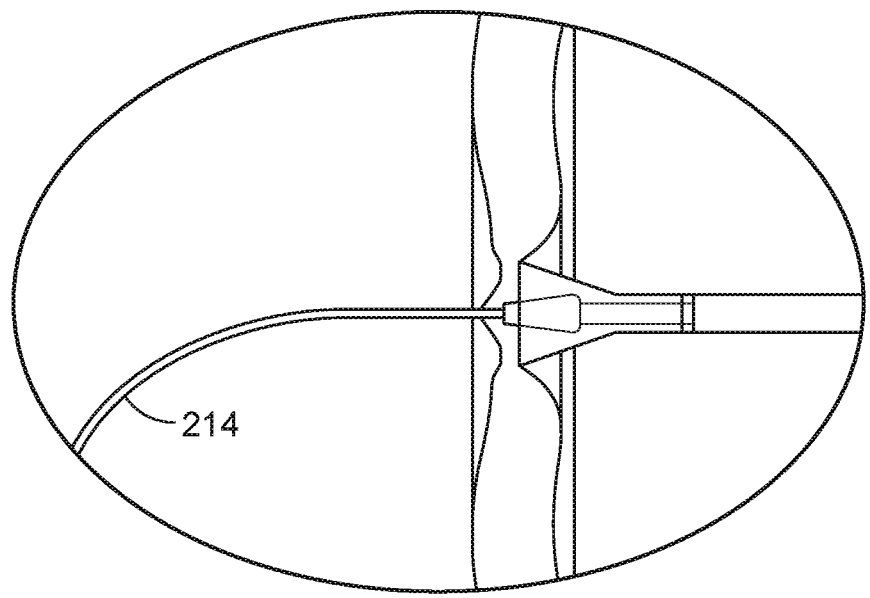
Figure 40H:
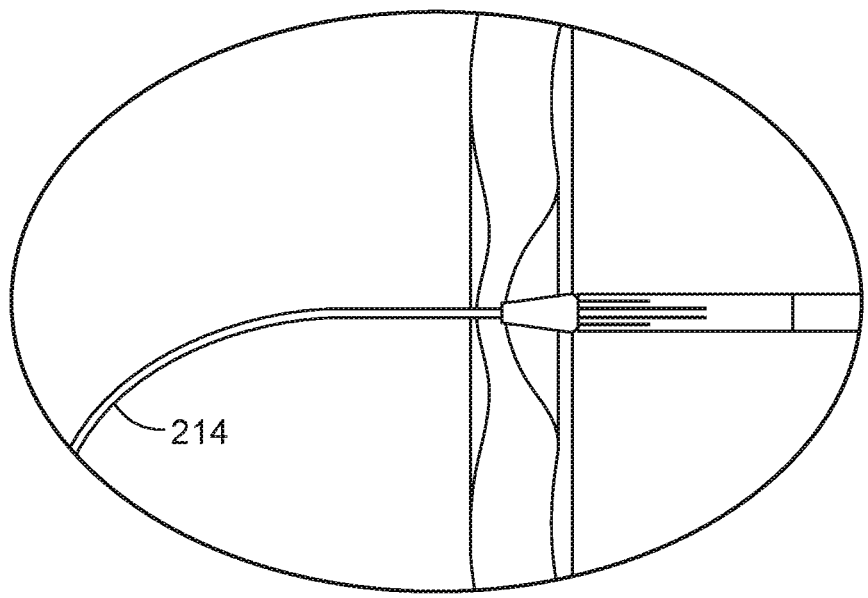
Figure 40I:
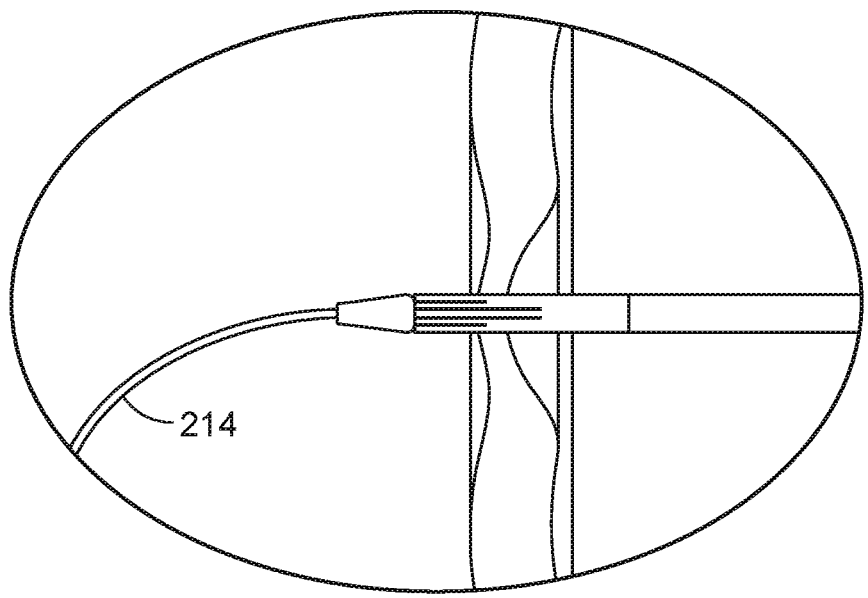
Figure 40J:
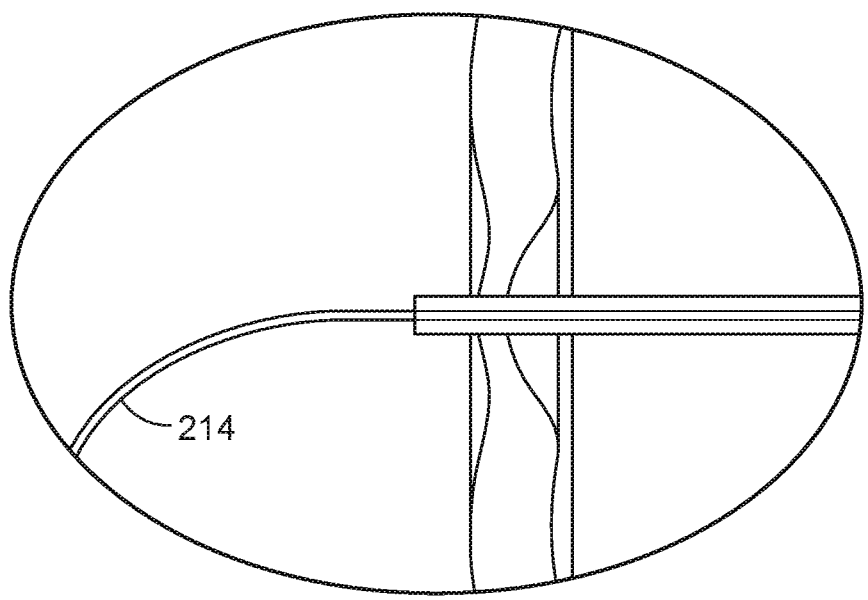

Needle 212 access is shown in FIG. 40E, followed by guidewire 214 deployment in FIG. 40F. The needle is retracted in FIG. 40G, and suction is stopped and the funnel retracted/collapsed in FIG. 40H. Pushing the sheath forward may recapture the funnel/cone. Dilation may be performed (FIG. 40I), i.e., moving the sheath forward with the bullet tip may provide a dilation function, and the device may then be removed as in FIG. 40J, in some cases leaving the TS sheath in place, along with the guidewire if desired.

Advantages of implementations according to present principles may include one or more of the following. Systems and methods allow even physicians to single-handedly effectively manipulate the catheter to allow TS access. The system is fast and easy to deliver. For TS access, it is expected to take less than 20 min to obtain left atrial access for most physicians.

The invention claimed is:

1. An assembly for transseptal access, comprising:
   a steerable sheath including an elongated member having a proximal end and a distal end;
   an inflatable funnel coupled to and surrounding the elongated member at the distal end, the inflatable funnel substantially collapsed against the elongated member in a retracted configuration, the inflatable funnel further having an inflated configuration having a proximal end with a first radius and a distal end with a second radius, the second radius greater than the first radius, the inflated configuration caused by inflation through an inflation lumen;
   such that the elongated member and the inflatable funnel are configured to be delivered to a septal location, and such that upon inflation the funnel is configured to transition from the retracted configuration to the inflated configuration; and
   a piercing element movable in distal and proximal directions through the elongated member, the piercing element configured to pierce the septum when the funnel is in the inflated configuration and when the funnel is contacting the septum, the piercing element including an activatable radio frequency element,
   such that the inflatable funnel provides a stable base for a transseptal puncture to occur, and is stiff when inflated but collapsible during delivery and retraction and wherein the inflatable funnel is comprised of a soft durometer polymer and is formed by folding the polymer back on itself.

2. The assembly of claim 1, wherein the first radius is between about 3 French to 10 French and the second radius is between about 2.5 mm and 15 mm.

3. The assembly of claim 2, wherein the first radius is between about 5 French to 8 French and the second radius is between about 5 mm and 10 mm.

4. The assembly of claim 1, wherein the elongated member or the funnel or the piercing element further comprises a radioopaque element.

5. The assembly of claim 1, wherein the assembly further comprises a dilator.

6. The assembly of claim 1, wherein the elongated member has further defined a guidewire lumen therein, the guidewire lumen extending from the proximal end to the distal end.

7. The assembly of claim 1, wherein the piercing element is on a distal end of a dilator, is hollow, or is disposed off-axis relative to an axis of the elongated member.

8. The assembly of claim 1, further comprising a governor configured to move the piercing element against the septum and to inhibit movement of the piercing element past a pre-specified point.

9. The assembly of claim 1, wherein the polymer of the inflatable funnel has a memory or an inherent geometric shape, to help the inflatable funnel deploy into the inflated configuration upon inflation.

10. The assembly of claim 1, further comprising an ultrasound element to visualize transseptal access locations prior to puncture.

11. The assembly of claim 1, wherein the piercing element is coupled to a reinforced polymer to transmit forces such as a push and pull needed for puncture.

12. The assembly of claim 1, wherein the distal end of the transseptal assembly includes a metallic band encircling a polymer tip, or includes a radioopaque compounded polymer.

13. An assembly for transseptal access, comprising:
   a steerable sheath including an elongated member having a proximal end and a distal end; and
   an inflatable funnel coupled to and substantially surrounding the elongated member at the distal end, the inflatable funnel substantially collapsed against the elongated member in a retracted configuration, the inflatable funnel further having an expanded configuration when inflated through an inflation lumen, the expanded configuration having a proximal end with a first radius and a distal end with a second radius, the second radius greater than the first radius; and
   a piercing element including an activatable radio frequency element disposed on a dilator movable in distal and proximal directions through the elongated member, the radio frequency element configured to puncture transseptal tissue when activated,
   such that the inflatable funnel provides a stable base for a transseptal puncture to occur, and is stiff when inflated but collapsible during delivery and retraction, wherein the inflatable funnel is comprised of a soft durometer polymer, and wherein the inflatable funnel is formed by folding the polymer back on itself.

14. The assembly of claim 13, wherein the elongated member or the funnel or the piercing element further comprises a radioopaque element.

15. The assembly of claim 13, wherein the piercing element is hollow or is disposed off-axis relative to an axis of the dilator.

16. The assembly of claim 13, further comprising a governor configured to move the piercing element against the septum and to inhibit movement of the piercing element past a pre-specified point.

17. The assembly of claim 13, wherein the polymer of the inflatable funnel has a memory or an inherent geometric shape, to help the inflatable funnel deploy into the inflated funnel configuration upon inflation.

* * * * *